(12) United States Patent
Kobayashi et al.

(10) Patent No.: US 7,824,872 B2
(45) Date of Patent: Nov. 2, 2010

(54) PHARMACEUTICAL AGENTS

(75) Inventors: Masanobu Kobayashi, Sapporo (JP); Jian Chen, Sapporo (JP)

(73) Assignee: Theravalues Corporation, Tokyo (JP)

( * ) Notice: Subject to any disclaimer, the term of this patent is extended or adjusted under 35 U.S.C. 154(b) by 0 days.

(21) Appl. No.: 10/551,866

(22) PCT Filed: Apr. 5, 2004

(86) PCT No.: PCT/JP2004/004917

§ 371 (c)(1), (2), (4) Date: Sep. 28, 2006

(87) PCT Pub. No.: WO2004/090158

PCT Pub. Date: Oct. 21, 2004

(65) Prior Publication Data

US 2007/0031899 A1 Feb. 8, 2007

Related U.S. Application Data

(60) Provisional application No. 60/459,644, filed on Apr. 3, 2003.

(51) Int. Cl.
G01N 33/53 (2006.01)
(52) U.S. Cl. .................. 435/7.23; 530/387.1
(58) Field of Classification Search .......... None
See application file for complete search history.

(56) References Cited

U.S. PATENT DOCUMENTS

| 5,871,960 | A | 2/1999 | Smith et al. | |
| 7,268,136 | B2 * | 9/2007 | Green et al. | 514/248 |
| 7,318,924 | B2 | 1/2008 | McKenzie et al. | |
| 2004/0146942 | A1 | 7/2004 | Weihe et al. | |

FOREIGN PATENT DOCUMENTS

| WO | WO 02/077033 | 10/2002 |
| WO | WO 02/093173 | 11/2002 |

OTHER PUBLICATIONS

Mizuno et al. (BBRC vol. 281, pp. 663-669, 2001).*
Wang et al. (Archives of Biochemistry and Biophysics, vol. 390, pp. 9-18, 2001).*
Apantaku LM. Breast cancer diagnosis and screening, American Family Physician (2000). (Electronic version, downloaded from http://www.healthlibrary.com/doctors2/breastcancer2.html).*
Martin et al (Journal of the National Cancer Institute, 92:1126-1135, 2000).*
Whitmarsh et al. (Methods in Enzymology, vol. 332, pp. 319-336, 2001).*
Luo, "Current research status of small molecular polypeptides antagonizing or mimicking cytokine activities," *Foreign Medical Science*, 2002, 25(3):121-125 (English-language summary included).
Brown, "Exploiting the hypoxic cancer cell: mechanisms and therapeutic strategies," *Mol. Med. Today*, 2000, 61:157-162.
Brown and Giaccia, "The Unique Physiology of Solid Tumors: Opportunities (and Problems) for Cancer Therapy," *Cancer Res.*, 1998, 58:1408-1416.
Comerford et al., "Hypoxia-inducible Factor-1-dependent Regulation of the Multidrug Resistance (*MDR1*) Gene," *Cancer Res.*, 2002, 62:3387-3394.
Cuypers et al., "Murine Leukemia Virus-Induced T-Cell Lymphomagenesis: Integration of Proviruses in a Distinct Chromosomal Region," *Cell*, 1984, 37:141-150.
Dhanasekaran et al., "Delineation of prognostic biomarkers in prostate cancer," *Nature*, 2001, 412:822-826.
Luk et al., "Effect of Transient Hypoxia on Sensitivity to Doxorubicin in Human and Murine Cell Lines," *J. Natl. Cancer Inst.*, 1990, 82:684-692.
Möröy et al., "Expression of a *Pim-1* transgene accelerates lymphoproliferation and inhibits apoptosis in *lpr/lpr* mice," *Proc. Natl. Acad. Sci. USA*, 1993, 90:10734-10738.
Niizeki et al., "Hypoxia enhances the expression of autocrine motility factor and the motility of human pancreatic cancer cells," *Br. J. Cancer*, 2002, 86:1914-1919.
Sakata et al., "Hypoxia-induced drug resistance: comparison to P-glycoprotein-associated drug resistance," *Br. J. Cancer*, 1991, 64:809-814.
Sanna and Rofstad, "Hypoxia-Induced Resistance to Doxorubicin and Methotrexate in Human Melanoma Cell Lines In Vitro," *Int. J. Cancer*, 1994, 58:258-262.
Selten et al., "Proviral activation of the putative oncogene *Pim*-1 in MuLV induced T-cell lymphomas," *EMBO J.*, 1985, 4(7):1793-1798.
Teh, "Pim-1 induced by hypoxia is involved in drug resistance and tumorigenesis of solid tumor cells," *Hokkaido Igaku Zasshi*, 2004, 79:19-23, 25-26.
Teicher, "Hypoxia and drug resistance," *Cancer Metastasis Rev.*, 1994, 13:139-168.
Verbeek et al., "Mice Bearing the Eµ-*myc* and Eµ-*pim*-1 Transgenes Develop Pre-B-Cell Leukemia Prenatally," *Mol. Cell. Biol.*, 1991, 11(2):1176-1179.
Wang et al., "Pim-1: A serine/threonine kinase with a role in cell survival, proliferation, differentiation and tumorigenesis," *J. Vet. Sci.*, 2001, 2(3):167-179.
Zakut-Houri et al., "The cDNA sequence and gene analysis of the human *pim* oncogene," *Gene*, 1987, 54:105-111.

* cited by examiner

*Primary Examiner*—Larry R. Helms
*Assistant Examiner*—Meera Natarajan
(74) *Attorney, Agent, or Firm*—Fish & Richardson P.C.

(57) ABSTRACT

An objective of the present invention is to provide methods of screening for novel compounds that exhibit anticancer activity. The screening methods of the present invention comprise using serine/threonine kinase Pim-1, or partial peptides or salts thereof.

9 Claims, 14 Drawing Sheets

ALLN: (A CALPAIN INHIBITOR I)
INHIBITOR OF PROTEASES AND PROTEASOME

IP: ANTI-Ub ANTIBODY

Ub-Pim-1    Ub-PROTEINS

TREATED BY ALLN
(PROTEASOME-
INHIBITOR)
FOR 16 HOURS
1:   0 μM
2:  50 μM
3:100 μM

IB: ANTI-Pim-1    IB: ANTI-Ub

PHARMACEUTICAL AGENTS

CROSS-REFERENCE TO RELATED APPLICATIONS

This application is a National Stage application under 35 U.S.C. §371 and claims benefit under 35 U.S.C. §119(a) of International Application No. PCT/JP04/004917 having an International Filing Date of Apr. 5, 2004, which claims the benefit of priority of U.S. Application No. 60/459,644 having a filing date of Apr. 3, 2003.

TECHNICAL FIELD

The present invention relates to methods of screening for therapeutic and preventive agents for cancer, and more specifically, relates to methods of screening for therapeutic and preventive agents for cancer, in which these agents are also effective against cancer cells and solid cancers for which anticancer agents have become ineffective.

BACKGROUND ART

Many types of anticancer agents are currently in clinical use. These clinically applied anticancer agents encounter many problems, such as the emergence of cancer cells that have acquired resistance to once-effective anticancer agents, lowering their efficacy toward solid cancers. The efficacy of anticancer agents against solid tumors is thought to decrease as the inner part of a solid tumor becomes hypoxic when it reaches a certain size or larger.

In progressive cancers, the inner cancer cells proliferate faster than surrounding cells. The supply of new blood vessels to these inner cells thus becomes inadequate, blood supply becomes insufficient, and hypoxic conditions result. For example, in Teicher, B. A. "Hypoxia and drug resistance." Cancer Metastasis Rev., 13:139-168, 1994; Brown, J. M. & Giaccia, A. J. "The unique physiology of solid tumors: opportunities (and problems) for cancer therapy." Cancer Res., 58:1408-1416, 1998; Brown, J. M. "Exploiting the hypoxic cancer cell: mechanisms and therapeutic strategies." Mol. Med. Today, 6:157-162, 2000; Luk, C. K., Veinot-Drebot, L., Tjan, E. & Tannock, I. F. "Effect of transient hypoxia on sensitivity to doxorubicin in human and murine cell lines." J. Natl. Cancer Inst., 82:684-692, 1990; Sakata, K., Kwok, T. T., Murphy, B. J., Laderoute, K. R., Gordon, G. R., Sutherland, R. M. "Hypoxia-induced drug resistance: comparison to P-glycoprotein-associated drug resistance." Br. J. Cancer, 64:809-814, 1991; Sanna, K. & Rofstad, E. K. "Hypoxia-induced resistance to doxorubicin and methotrexate in human melanoma cell lines in vitro." Int. J. Cancer, 58:258-262, 1994, it is disclosed that cancer cells in apoxic conditions are more resistant to chemotherapy and radiation therapy than cancer cells under high-oxygen conditions, and that apoxic conditions induce drug resistance in solid cancer cells. The results described in the above-mentioned literature show that apoxic conditions induce anti-apoptosis factors in solid cancer cells.

Pim-1 is a serine/threonine kinase initially identified in T cell lymphomas caused by murine leukemia virus (MuLV) as a gene frequently activated by leukemia virus insertion (Cuypers, H. T., Selten, G., Quint, W., Zijlstra, M., Maandag, E. R., Boelens, W., van Wezenbeek, P., Melief, C., Berns, A. "Murine leukemia virus-induced T-cell lymphomagenesis: integration of proviruses in a distinct chromosomal region." Cell, 37:141-150, 1984; and Selten, G., Cuypers, H. T. & Berns, A. "Proviral activation of the putative oncogene Pim-1 in MuLV induced T-cell lymphomas." EMBO J, 4:1793-1798, 1985. Further, Pim-1 in the cytoplasm has been reported to function as a factor for inhibiting apoptosis in various hematopoietic cells (Pircher, T. J., et al. "Pim-1 kinase protects hematopoietic FDC cells from genotoxin-induced death." Oncogene, 19:3684-3692, 2000; and Lilly, M. & Kraft, A. "Enforced expression of the Mr 33,000 Pim-1 kinase enhances factor-independent survival and inhibits apoptosis in murine myeloid cells." Cancer Res., 57:5348-5355, 1997. Therefore, substances that can inactivate Pim-1 would be effective for preventing/treating solid cancers, and various Pim-1-induced disorders.

Therefore, an objective of the present invention is to provide methods of screening for novel compounds that exhibit anticancer activity. Another objective of the present invention is to provide methods of screening for preventive and therapeutic agents for cancer, in which the agents prevent and treat cancer by inactivating Pim-1.

DISCLOSURE OF THE INVENTION

As a result of extensive study to accomplish the above-mentioned objectives, the present inventors found a protein present in large amounts in cancer cells, and completed the present invention based on this finding.

The present invention was made based on the above-mentioned finding, and provides methods of screening for preventive and therapeutic agents for cancer, wherein the methods comprise using serine/threonine kinase Pim-1 or partial peptides or salts thereof.

The present invention also provides kits for screening for preventive and therapeutic agents for cancer, wherein the kits comprise serine/threonine kinase Pim-1, or partial peptides or salts thereof.

The present invention also provides preventive and therapeutic agents for cancer, wherein the agents are obtained using an above-described screening method or kit.

The present invention also provides preventive and therapeutic agents for cancer, wherein the agents comprise compounds, or salts of these compounds, that inhibit the activity of the serine/threonine kinase Pim-1, or partial peptides or salts thereof.

The present invention also provides preventive and therapeutic agents for cancer, wherein the agents comprise compounds, or salts of these compounds, that inhibits the expression of genes encoding serine/threonine kinase Pim-1 or partial peptides or salts thereof.

The present invention also provides preventive and therapeutic agents for cancer, wherein the agents comprise polypeptides comprising amino acid sequences identical to or substantially identical to polypeptides comprising the amino acid sequence of SEQ ID NO: 3.

The present invention also provides preventive and therapeutic agents for cancer, wherein the agents comprise antibodies against serine/threonine kinase Pim-1 or partial peptides or salts thereof.

The present invention also provides methods of screening for apoptosis-inducing agents, wherein the methods comprise using serine/threonine kinase Pim-1 or partial peptides or salts thereof.

The present invention also provides kits for screening for apoptosis-inducing agents, wherein the agents comprise serine/threonine kinase Pim-1 or partial peptides or salts thereof.

The present invention also provides apoptosis-inducing agents obtained using the above-described screening methods or kits.

The present invention also provides apoptosis-inducing agents, which comprise compounds, or salts of these compounds, that inhibit the activity of serine/threonine kinase Pim-1 or partial peptides or salts thereof.

The present invention also provides apoptosis-inducing agents that comprise compounds, or salts of these compounds, that inhibit the expression of genes encoding serine/threonine kinase Pim-1 or partial peptides or salts thereof.

The present invention also provides apoptosis-inducing agents that comprise polypeptides comprising amino acid sequences identical to or substantially identical to polypeptides comprising the amino acid sequence of SEQ ID NO: 3.

The present invention also provides apoptosis-inducing agents that comprise antibodies against serine/threonine kinase Pim-1 or partial peptides or salts thereof.

The present invention also provides methods of screening for anticancer agent potentiators, wherein the methods comprise using serine/threonine kinase Pim-1 or partial peptides or salts thereof.

The present invention also provides kits for screening for anticancer agent potentiators, wherein the kits comprise serine/threonine kinase Pim-1 or partial peptides or salts thereof.

The present invention also provides anticancer agent potentiators, wherein the potentiators are obtained using the above-described screening methods or kits.

The present invention also provides anticancer agent potentiators, wherein the potentiators comprise compounds, or salts of these compounds, that inhibit serine/threonine kinase Pim-1 or partial peptides or salts thereof.

The present invention also provides anticancer agent potentiators, wherein the potentiators comprise compounds, or salts of these compounds, that inhibit the expression of genes expressing serine/threonine kinase Pim-1 or partial peptides or salts thereof.

The present invention also provides anticancer agent potentiators, wherein the potentiators comprise polypeptides comprising amino acid sequences identical to or substantially identical to polypeptides comprising the amino acid sequence of SEQ ID NO: 3.

The present invention also provides anticancer agent potentiators, wherein the potentiators comprise antibodies against serine/threonine kinase Pim-1 or partial peptides or salts thereof.

The present invention also provides polynucleotides comprising nucleotide sequences having homology of at least 95% or more to:

(a) a polynucleotide comprising the nucleotide sequence of SEQ ID NO: 4, or a cDNA polynucleotide that can hybridize to a polynucleotide comprising the nucleotide sequence of SEQ ID NO: 4; and (b) a polynucleotide comprising a nucleotide sequence that encodes a polypeptide comprising an amino acid sequence identical to or substantially identical to the amino acid sequence of SEQ ID NO: 3, or a cDNA polynucleotide that can hybridize with a polynucleotide comprising a nucleotide sequence that encodes a polypeptide comprising an amino acid sequence identical to or substantially identical to the amino acid sequence of SEQ ID NO: 3.

The present invention also provides recombinant vectors comprising the above-described polynucleotides.

The present invention also provides host cells carrying the above-described expression vectors.

The present invention also provides methods for producing polypeptides or salts thereof that comprise amino acid sequences identical to or substantially identical to the amino acid sequence of SEQ ID NO: 3, wherein the methods comprise the step of culturing the above-described host cells under conditions suitable for expression of the polypeptide, to collect the polypeptide from the obtained culture.

The present invention also provides preventive and therapeutic agents for cancer, wherein the agents comprise the above-described polynucleotides or recombinant vectors.

The present invention also provides apoptosis-inducing agents that comprise the above-described polynucleotides or recombinant vectors.

The present invention also provides anticancer agent potentiators, wherein the potentiators comprise the above-described polynucleotides or recombinant vectors.

BEST MODE FOR CARRYING OUT THE INVENTION

Figure 1:
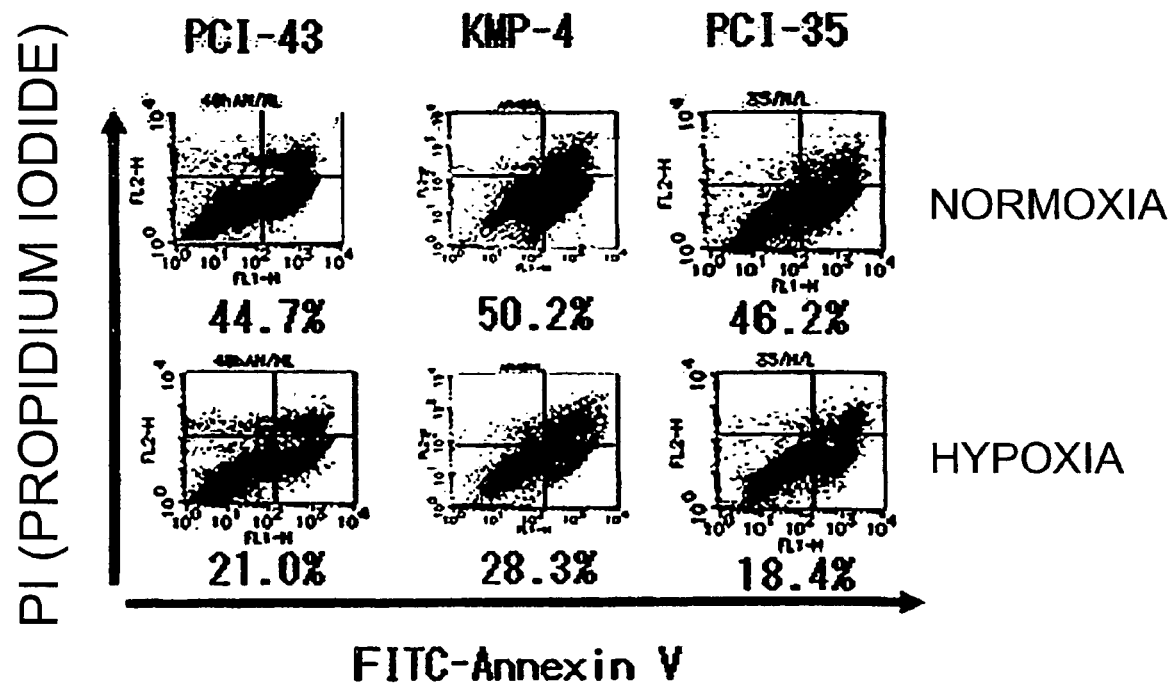
FIG. 1 shows the results of FACS analysis.

The present invention is described below.

In the present invention, "serine/threonine kinase Pim-1" (hereinafter also referred to as "Pim-1") means a polypeptide comprising the amino acid sequence of SEQ ID No: 1, and having serine/threonine kinase activity. Pim-1 was identified in T cell lymphomas caused by murine leukemia virus (MuLV) as a gene that is activated by MuLV insertion (Cuypers, H. T., Selten, G., Quint, W., Zijlstra, M., Maandag, E. R., Boelens, W., van Wezenbeek, P., Melief, C., Berns, A. "Murine leukemia virus-induced T-cell lymphomagenesis: integration of proviruses in a distinct chromosomal region." Cell, 37:141-150, 1984; and Selten, G., Cuypers, H. T. & Berns, A. "Proviral activation of the putative oncogene Pim-1 in MuLV induced T-cell lymphomas." EMBO J, 4:1793-1798, 1985.

In the present invention, Pim-1 or partial peptides thereof include proteins that comprise an amino acid sequence identical to, or substantially identical to the amino acid sequence of SEQ ID No: 1. These proteins may be those derived from cells (for example, hepatocytes, splenocytes, neurons, glial cells, pancreatic β cells, myeloid cells, mesangial cells, Langerhans' cells, epidermal cells, epithelial cells, goblet cells, endothelial cells, smooth muscle cells, fibroblasts, fibrocytes, myocytes, adipocytes, immunocytes (such as macrophages, T cells, B cells, natural killer cells, mast cells, neutrophils, basophils, eosinophils, monocytes, etc.), megakaryocytes, synoviocytes, chondrocytes, osteocytes, osteoblasts, osteoclasts, mammary cells, hepatocytes, or interstitial cells, or precursor cells, stem cells, or cancer cells thereof) of humans or warm-blooded animals (for example, guinea pigs, rats, mice, chickens, rabbits, pigs, sheep, cattle, monkeys, etc.), or from various tissues where such cells exist, such as the brain, various parts of the brain (for example, the olfactory bulb, amygdaloid nucleus, basal ganglion, hippocampus, thalamus, hypothalamus, cerebral cortex, medulla oblongata, or cerebellum), spinal cord, pituitary gland, stomach, pancreas, kidney, liver, gonads, thyroid, gall bladder, bone marrow, adrenal gland, skin, muscles, lungs, gastrointestinal tract (for example, large intestine, and small intestine), blood vessels, heart, thymus, spleen, submandibular gland, peripheral blood, prostate gland, testes, ovaries, placenta, uterus, bones, joints, and skeletal muscles, or they may be synthetic proteins.

An amino acid sequence that is substantially identical to the amino acid sequence of SEQ ID No: 1 is, for example, an amino acid sequence with sequence homology to the amino acid sequence of SEQ ID No: 1 of approximately 50% or more, preferably approximately 60% or more, more preferably approximately 70% or more, even more preferably approximately 80% or more, especially preferably approximately 90% or more, and most preferably approximately 95% or more. Preferably, the proteins comprising amino acid sequences substantially identical to the amino acid sequence of SEQ ID No: 1 are, for example, proteins comprising amino acid sequences substantially identical to the amino acid sequence of SEQ ID No: 1, and with substantially the same type of activity as a protein comprising the amino acid sequence of SEQ ID No: 1.

"Substantially the same type of activity" refers to, for example, the serine/threonine kinase activity possessed by Pim-1. Activities equivalent to this kinase activity are preferred. This kinase activity can be measured, for example, as the activity of phosphorylating substrate peptides such as p21 protein or myb protein. Furthermore, since Pim-1 suppresses apoptosis-inducing activity, as described below, activities can be determined to be substantially equivalent or otherwise by measuring this effect of suppressing apoptosis-inducing activity.

Pim-1 used in the present invention includes, for example, proteins comprising an amino acid sequence with one or two or more (for example, 1 to 50 or so, or preferably 1 to 30 or so) amino acid deletions in the amino acid sequence of SEQ ID No: 1; proteins comprising an amino acid sequence with one or two or more (for example, 1 to 100 or so, or preferably 1 to 30 or so) amino acid additions in the amino acid sequence of SEQ ID No: 1; proteins comprising an amino acid sequence with one or two or more (for example, 1 to 100 or so, or preferably 1 to 30 or so) amino acid insertions in the amino acid sequence of SEQ ID No: 1; peptides comprising an amino acid sequence with one or two or more (for example, 1 to 100 or so, or preferably 1 to 30 or so) amino acid substitutions in the amino acid sequence of SEQ ID No: 1; or proteins comprising an amino acid sequence with combinations of the above-mentioned alterations. The positions of these amino acid insertions, substitutions, and deletions are not particularly limited.

The C-terminus of a protein comprising the amino acid sequence of SEQ ID No: 1 may be a carboxyl group (—COOH), a carboxylate group (—COO⁻), an amide group (—CONH$_2$), or an ester group (—COOR). R in the ester group includes, for example, an alkyl group of 1 to 6 carbon atoms such as a methyl group, an ethyl group, an n-propyl group, an isopropyl group, or an n-butyl group; a cycloalkyl group of 3 to 8 carbon atoms such as a cyclopentyl group or a cyclohexyl group; an aryl group of 6 to 12 carbon atoms such as a phenyl group, or an α-naphthyl group; a phenyl-alkyl group such as a benzyl group or a phenethyl group; an α-naphthyl-alkyl group such as an α-naphthylmethyl group; an aralkyl group of 7 to 14 carbon atoms; and a pivaloyloxymethyl group. When the protein represented by SEQ ID No: 1 has carboxyl groups (or carboxylate groups) besides the one at the C terminus, those carboxyl groups may be amidated or esterified. These esters include, for example, the esters described above for the C terminus. Furthermore, the proteins represented by SEQ ID No: 1 may be the following: proteins in which the amino group of the N-terminal amino acid residue (for example, the methionine residue) is protected by a protecting group (such as an acyl group of 1 to 6 carbon atoms, such as an alkanoyl group of 1 to 6 carbon atoms that includes a formyl group or an acetyl group); proteins in which the N-terminal glutamine residue, which is produced by cleavage in vivo, is converted to a pyroglutamate; or proteins in which the substituents on the side chains of amino acids in the molecule (—OH, —SH, an amino group, an imidazole group, an indole group, a guanidinio group, or such) are protected by appropriate protecting groups (for example, an acyl group of 1 to 6 carbon atoms, such as an alkanoyl group of 1 to 6 carbon atoms that includes a formyl group or an acetyl group); or conjugated proteins such as sugar-chain-linked so-called glycoproteins.

The partial peptides of Pim-1 used in the present invention are partial peptides of the aforementioned proteins, and are preferably any partial peptides with properties similar to the aforementioned proteins.

The salts of Pim-1 or partial peptides thereof used in the present invention include salts formed with physiologically acceptable acids (such as inorganic acids, and organic acids), and bases (for example, alkali metal salts), and in particular, physiologically acceptable acid-added salts are preferred. Examples of such salts include those with inorganic acids (for example, hydrochloric acid, phosphoric acid, hydrobromic acid, and sulfuric acid) and with organic acids (for example, acetic acid, formic acid, propionic acid, fumaric acid, maleic acid, succinic acid, tartaric acid, citric acid, malic acid, oxalic acid, benzoic acid, methanesulfonic acid, and benzenesulfonic acid). Pim-1 or partial peptides or salts thereof used in the present invention can be prepared by known protein purification methods from the aforementioned cells or tissues of humans or warm-blooded animals. Furthermore, they can be produced by culturing transformants comprising DNAs encoding the proteins (for example, DNAs comprising the nucleotide sequence of SEQ ID No: 2). Furthermore, they can be produced according to well known peptide synthesis methods. Production from tissues or cells of humans or mammals comprises the steps of homogenizing the tissues or cells of humans or mammals, then extracting the homogenate using an acid or such, and then purifying and isolating the protein from the obtained extract by combining chromatographic procedures such as reverse phase chromatography and ion exchange chromatography.

Pim-1 or partial peptides or salts thereof used in the present invention may be synthesized, and ordinary commercially available resins for protein synthesis may be used for the synthesis. Examples of such resins include chloromethyl resin, hydroxymethyl resin, benzhydrylamine resin, aminoethyl resin, 4-benzyloxybenzyl alcohol resin, 4-methylbenzhydrylamine resin, PAM resin, 4-hydroxymethylmethylphenyl acetoamidomethyl resin, polyacrylamide resin, 4-(2',4'-dimethoxyphenyl-hydroxymethyl)phenoxy resin and 4-(2',4'-dimethoxyphenyl-Fmoc aminoethyl)phenoxy resin. Using such resins, amino acids in which the α-amino group and functional groups on the side chains are suitably protected are condensed on the resin using various well known condensation methods, in accordance with the sequence of the target protein. At the end of the reaction, the protein or partial peptide is excised from the resin, and at the same time, the various protective groups are removed to obtain the desired protein, or partial peptide thereof, or salt thereof. The above-mentioned protected amino acids can be condensed using various activating reagents that may be used for protein synthesis, and carbodiimides are particularly suitable. The carbodiimides used include DCC, N,N'-diisopropylcarbodiimide, and N-ethyl-N'-(3-dimethylaminoprolyl)carbodiimide. For activation by carbodiimide, either the protected amino acids can be added directly to the resin together with a racemization inhibitor (such as HOBt, or HOOBt), or the protected amino acids can be first activated either as symmetrical acid anhydrides, or HOBt ester, or HOOBt ester, and then added to the resin.

The solvents used in activating the protected amino acids and condensing them with the resin may be selected as needed from known solvents for use in protein condensation reactions. For example, acid amides such as N,N-dimethylformamide, N,N-dimethylacetoamide, and N-methylpyrolidone; halogenated hydrocarbons such as methylene chloride and chloroform; alcohols such as trifluoroethanol; sulfoxides such as dimethylsulfoxide; pyridine; ethers such as dioxane and tetrahydrofuran; nitriles such as acetonitrile and propionitrile; esters such as methyl acetate and ethyl acetate; or appropriate mixtures thereof can be used. A reaction temperature can be selected appropriately from the range known to be applicable for protein bond-forming reactions, and normally a temperature between approximately −20° C. and 50° C. is appropriately selected. The activated amino acid derivatives are ordinarily used 1.5 to 4 times in excess. If the results of tests using ninhydrine reaction show insufficient condensation, sufficient condensation can be achieved by repeating the condensation reaction without removing the protective groups. If sufficient condensation is not achieved even on repeating the reaction, the unreacted amino acids can be acetylated with acetic anhydride or acetylimidazole to avoid an effect on the subsequent reactions.

Protective groups used for the starting amino groups include, for example, Z, Boc, t-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, and Fmoc. Carboxyl groups can be protected for example by alkyl esterification (for example, straight-chain, branched, or cyclic alkylesterification of methyl, ethyl, propyl, butyl, t-butyl, cyclopentyl, cyclohexyl, cycloheptyl, cyclooctyl or 2-adamantyl, and such), aralkyl esterification (for example, esterification to benzyl ester, 4-nitrobenzyl ester, 4-methoxybenzyl ester, 4-chlorobenzyl ester or benzhydryl ester), phenacyl esterification, benzyloxycarbonyl hydrazidification, t-butoxycarbonyl hydrazidification or trityl hydrazidification. The hydroxyl group of serine can be protected by esterification or etherification. Groups that are suitable for esterification include, for example, lower (1 to 6 carbon atoms) alkanoyl groups such as acetyl groups, aroyl groups such as benzoyl groups, and substituents derived from carbonic acid such as benzyloxycarbonyl groups and ethoxycarbonyl groups. Substituents that are suitable for etherification include, for example, a benzyl group, a tetrahydropyranyl group, and a t-butyl group. Bzl, Cl$_2$-Bzl, 2-nitrobenzyl, Br—Z, t-butyl groups, and such can be used to protect the phenolic hydroxyl group of tyrosine. Tos, 4-methoxy-2,3,6-trimethylbenzenesulfonyl, DNP, benzyloxymethyl, Bum, Boc, Trt, Fmoc groups, and such can be used to protect the imidazole moiety of histidine.

Examples of activated carboxyl groups in the starting materials include corresponding acid anhydrides, azides, activated esters [esters with alcohols (such as pentachlorophenol, 2,4,5-trichlorophenol, 2,4-dinitrophenol, cyanomethyl alcohol, paranitrophenol, HONB, N-hydroxysuccimide, N-hydroxyphthalimide, or HOBt)], and such. Examples of activated amino groups in the starting materials include corresponding phosphoric acid amides. Methods that may be used to remove (eliminate) the protecting groups include, for example, catalytic reduction under a stream of hydrogen gas in the presence of a catalyst such as Pd-black or Pd-carbon, treatment with an acid such as anhydrous hydrogen fluoride, methanesulfonic acid, trifluoromethanesulfonic acid, trifluoroacetic acid or a mixture thereof, treatment with a base such as diisopropylethylamine, triethylamine, piperidine, or piperazine, or reduction with sodium in liquid ammonia. Elimination reactions using acid treatment as described above are generally performed at temperatures of approximately −20° C. to 40° C. Addition of cationic scavengers such as anisole, phenol, thioanisole, metacresol, paracresol, dimethylsulfide, 1,4-butanedithiol, and 1,2-ethanedithiol is effective in the acid treatment. Moreover, the 2,4-dinitrophenyl group used in protecting the imidazole group of histidine can be removed by thiophenol treatment, while the formyl group which is used in protecting the indole group of tryptophan can be removed by the aforementioned acid treatment in the presence of 1,2-ethanedithiol, 1,4-butanedithiol or such, as well as by treatment with an alkali such as a dilute sodium hydroxide solution, or dilute ammonia.

Protection of functional groups that should not participate in the reaction of starting materials, protecting groups, removal of protecting groups, and activation of functional groups that participate in the reaction, can be appropriately selected from well known substituent groups and means. In another method for obtaining an amide of a protein or partial peptide, for example, the α-carboxyl group of the carboxy terminal amino acid is first amidated for protection, the peptide (protein) chain is extended toward the amino group side to the desired chain length, a protein or a partial peptide in which only the N-terminal α-amino protective group of the peptide chain is removed and a protein or a partial peptide in which only the C-terminal carboxyl protective group of the peptide chain is removed are produced, and these proteins or peptides are condensed in a solvent mixture similar to that described above. The details of the condensation reaction are the same as described above. The protected protein or peptide obtained by condensation is purified, and then all protective groups can be removed by the aforementioned methods to obtain the desired crude protein or peptide. This crude protein or peptide can then be purified by various well-known purification methods, and the main fraction can be lyophilized to obtain an amide of the desired protein or peptide. To obtain an ester of the protein or peptide, the α-carboxyl group of the carboxy terminal amino acid is first condensed with a desired alcohol to produce an amino acid ester, and the desired ester of the protein or peptide can then be obtained in the same way as the amide of the protein or peptide.

The partial peptides of Pim-1, or salts thereof used in the present invention can be produced either according to known methods of peptide synthesis, or by cleaving Pim-1 used in the present invention with a suitable peptidase. Methods of peptide synthesis may include, for example, either solid phase synthesis or liquid phase synthesis. Specifically, partial peptides or amino acids that may constitute the partial peptides used in the present invention are condensed with the remaining portions, and if the product carries protective groups, the desired peptides can be produced by removing the protective groups.

The polynucleotides encoding Pim-1 used in the present invention can be any polynucleotides, as long as they comprise a nucleotide sequence encoding Pim-1. DNAs are preferred, and the DNAs may be genomic DNAs, genomic DNA libraries, cDNAs derived from the cells or tissues described above, cDNA libraries derived from the cells or tissues described above, or synthetic DNAs, or such. The vectors used for the libraries may be bacteriophages, plasmids, cosmids, phagemids, or such. In addition, the DNAs can be directly amplified by reverse transcriptase polymerase chain reaction (hereinafter abbreviated as "RT-PCR") using total RNA or mRNA fractions prepared from the cells or tissues described above. For example, the DNAs encoding Pim-1 used in the present invention may be any DNAs, as long as the DNAs comprise the nucleotide sequence of SEQ ID No: 2, or comprise a nucleotide sequence that hybridizes under highly stringent conditions with a DNA comprising the nucleotide sequence of SEQ ID No: 2, and the DNAs encode a protein with characteristics that are substantially the same as the aforementioned protein comprising the amino acid sequence encoded by the nucleotide sequence of SEQ ID No: 2.

The DNAs that can hybridize under highly stringent conditions with the nucleotide sequence of SEQ ID No: 2 include, for example, a DNA comprising a nucleotide sequence with approximately 50% or greater, preferably approximately 60% or greater, more preferably approximately 70% or greater, even more preferably approximately 80% or greater, particularly preferably approximately 90% or greater, or most preferably approximately 95% or greater homology with the nucleotide sequence of SEQ ID No: 2. Hybridization can be carried out using or in accordance with known methods that, for example, the methods described in "Molecular Cloning" 2nd edition (J. Sambrook et al., Cold Spring Harbor Lab. Press, 1989). When using a commercially available library, procedures can be performed according to the methods described in the attached instructions. More preferably, hybridization can be performed under highly stringent conditions. "Highly stringent conditions" refers to conditions such as a sodium concentration of 19 to 40 mM, or preferably 19 to 20 mM, and a temperature of 50 to 70° C., or preferably 60 to 65° C. Specifically, a sodium concentration of 19 mM and temperature of 65° C. are most preferable.

The DNAs encoding the partial peptide of Pim-1 used in the present invention may be any DNAs as long as they comprise a nucleotide sequence encoding a partial peptide used in the present invention. The DNAs used may be genomic DNAs, genomic DNA libraries, cDNAs derived from the cells or tissues described above, cDNA libraries derived from the cells or tissues described above, or synthetic DNAs. The DNAs encoding the partial peptides used in the present invention include, for example, DNAs carrying a portion of a DNA comprising the nucleotide sequence of SEQ ID No: 2, or DNAs that comprise a nucleotide sequence that hybridizes under highly stringent conditions with the nucleotide sequence of SEQ ID No: 2, and also comprises portions of DNAs that encode proteins with substantially the same activity as a protein of the present invention. The phrase, "a DNA that can hybridize with the nucleotide sequence of SEQ ID NO: 2" has the same meaning as described above. The above-described hybridization methods and highly stringent conditions are used.

Means for cloning the DNAs that completely encode Pim-1 and partial peptides thereof that are used in the present invention (hereinafter these may simply be referred to as "Pim-1") include using synthetic DNA primers comprising portions of the nucleotide sequence encoding Pim-1 to perform amplification by PCR, or selection by hybridization of DNAs incorporated into a suitable vector with a labeled DNA fragment encoding some or all regions of Pim-1, or a labeled synthetic DNA. Hybridization can be carried out by, for example, the methods described in "Molecular Cloning" 2nd edition (J. Sambrook et al., Cold Spring Harbor Lab. Press, 1989). When using commercially available libraries, procedures can be performed according to the methods described in the attached instructions. The nucleotide sequence of the DNAs can be changed using or in accordance with known methods, such as ODA-LAPCR, Gapped duplex, or Kunkel using PCR or known kits, for example, Mutan™-superExpress Km (Takara Shuzo Co., Ltd.), Mutan™-K (Takara Shuzo Co., Ltd.), or such. The cloned DNAs encoding the proteins can be used as is, depending on the purpose, or if desired, can be used after digestion with restriction enzymes, or after adding linkers. The DNAs may have an ATG as a translation initiation codon at their 5' end, and a TAA, TGA, or TAG as a translation termination codon at their 3' end. These translation initiation and termination codons may also be added to the DNAs using appropriate synthetic DNA adapters. The expression vectors for Pim-1 can be produced, for example, by (1) excising a DNA fragment of interest from a DNA encoding Pim-1, and then (2) ligating the DNA fragment downstream of a promoter in an appropriate expression vector.

The methods of screening for preventive and therapeutic agents for cancer of the present invention comprise using the abovementioned Pim-1 or partial peptides thereof, or salts thereof. More specifically, the methods of screening for preventive and therapeutic agents of the present invention can be carried out by contacting Pim-1 or a partial peptide thereof, or a salt thereof with a test substance, and measuring the phosphorylation activity of Pim-1. Alternatively, the methods can be carried out by contacting Pim-1, a partial peptide thereof, or a salt thereof with a test substance, and measuring the inhibitory effect of Pim-1 or the partial peptide or salt thereof on apoptosis induction.

In either case, the screening is performed by confirming the presence of an active substance by comparison with the activity observed in the absence of a test substance. Such methods also enable screening for apoptosis-inducing agents. Furthermore, inhibiting the activity of Pim-1 or a partial peptide or salt thereof can inhibit tumor formation; therefore, this method may allow screening for anticancer agent potentiators.

Examples of the test samples used in the screening methods of the present invention include cell extracts, plant extracts, purified or crude proteins, peptides, non-peptide compounds, synthetic low-molecular weight compounds, natural compounds, and gene libraries. The screening methods of the present invention may be carried out in cells, but can also be carried out in test tubes.

When carrying out the methods in cells, Pim-1-producing cells or cells transformed with a recombinant vector carrying a DNA encoding Pim-1 may be used. When carrying out the methods in test tubes, Pim-1 and a substrate peptide of Pim-1 are mixed in a suitable reaction buffer, and then the ability to phosphorylate is measured. There are no particular limitations on the substrate peptides, as long as they can be phosphorylated by Pim-1. The reaction conditions are those conventionally used for known kinases.

The above-mentioned recombinant vectors are described below.

A recombinant vector carrying a DNA encoding Pim-1 can be produced by ligating a nucleotide fragment encoding Pim-1 (for example, a polynucleotide comprising the nucleotide sequence of SEQ ID No: 2) downstream of a promoter in an appropriate expression vector. Suitable vectors for use in the present invention include plasmids derived from *Escherichia coli* (e.g., pBR322, pBR325, pUC18, or pUC118); plasmids derived from *Bacillus subtilis* (e.g., pUB110, pTP5, or pC194); plasmids derived from yeast (e.g., pSH19, or pSH15); bacteriophages, such as λ phage; and animal viruses, such as retrovirus, vaccinia virus, or baculovirus; as well as pA1-11, pXT1, pRc/CMV, pRc/RSV, pcDNAI/Neo. In the context of the present invention, any promoter may be used, so long as it is adapted for use in hosts used to express a gene of interest. For example, when the host is *E. coli*, preferred promoters are the trp promoter, lac promoter, recA promoter, λPL promoter, lpp promoter, T7 promoter, T3 promoter, and araBAD promoter. When the host belongs to the genus *Bacillus*, preferred promoters are the SPO1 promoter, penP promoter, XYL promoter, HWP promoter, and CWP promoter. When the host is *Bacillus subtilis*, preferred promoters are the SPO1 promoter, SPO2 promoter, and penP promoter. When the host is yeast, preferred promoters are the PHO5 promoter, PGK promoter, GAP promoter, and ADH promoter. When animal cells are used as the host, the SRα promoter, SV40 promoter, LTR promoter, CMV promoter, HSV-TK promoter, and such are preferably used. In addition, when insect cells are used as the host, the polyhedron promoter, OplE2 promoter, and such are used.

In addition to the above described promoters, the recombinant vectors may include known enhancers, splicing signals, poly(A) addition signals, selection markers, SV40 replication origins (sometimes abbreviated to "SV40orgdi" hereinafter), and such, as desired. Furthermore, if needed, the proteins encoded by a DNA of the present invention can also be expressed as fusion proteins with another protein (for example, glutathione-5-transferase and protein A). Such fusion proteins can be cleaved by using a site-specific protease to divide them into respective proteins.

Examples of the above-described selection marker include dihydrofolate reductase (hereinafter abbreviated as "dhfr") gene [methotrexate (MTX) resistant], ampicillin resistant (hereinafter abbreviated as "Amp$^r$") gene, and neomycin resistant (hereinafter abbreviated as "Neo$^r$"; G418 resistant) gene. In particular, when using dhfr-gene-deficient Chinese hamster cells, and using the dhfr gene as a selection marker, selection of a desired gene can be carried out in a thymidine-free medium.

Examples of suitable host cells include *Escherichia* bacteria, *Bacillus* bacteria, yeast, insect cells, insects, and animal cells. Specific examples of suitable *Escherichia* bacteria include *Escherichia coli* K12.DH1 (Proc. Natl. Acad. Sci. USA 60:160, 1968), JM103 (Nucleic Acids Research 9:309, 1981), JA221 (Journal of Molecular Biology 120:517, 1978)), HB101 (Journal of Molecular Biology 41:459, 1969), C600 (Genetics, 39:440, 1954), DH5α, and JM109. Examples of suitable *Bacillus* bacteria include *Bacillus subtilis* MI114 (Gene 24:255, 1983), 207-21 (Journal of Biochemistry 95:87, 1984), and *Bacillus brevis*. Examples of suitable yeasts include *Saccaromyces cerevisiae* AH22, AH22R-, NA87-11A, DKD-5D, 20B-12, *Schizosaccaromyces pombe* NCYC1913, NCYC2036, *Pichia pastoris* M71, and *Hansenula polymorpha*. Examples of the insect cells used include cell lines derived from *Spodoptera frugiperda* larvae (Sf cells), MG1 cells derived from the mid-intestine of *Trichoplusia ni*, High Five™ cells derived from eggs of *Trichoplusia ni*, cells derived from *Mamestra brassicae*, and cells derived from *Estigmena acrea* for the AcNPV virus. *Bombyx mori* N cells (BmN cells), and such are used for the BmNPV virus. Examples of the above-mentioned Sf cells that can be used include Sf9 cells (ATCC CRL1711), and Sf21 cells (both cells are described in Vaughn, J. L. et al., "In Vivo", 13:213-217, 1977). Insects that are used include, for example, *Bombyx mori* larvae (Maeda et al., Nature, 315:592, 1985). Examples of suitable mammalian cells include simian COS-7 cells, Vero cells, Chinese hamster ovary cells (hereinafter abbreviated to "CHO"), Chinese hamster ovary cells deficient in dhfr gene (hereinafter abbreviated to "CHO (dhfr$^-$)"), mouse L cells, mouse AtT-20 cells, mouse myeloma cells, rat GH3 cells, and human FL cells.

As necessary, a polynucleotide encoding a signal sequence appropriate to the host can be added to the 5'-end side of a polynucleotide encoding Pim-1. When using bacteria of the genus *Escherichia* as host cells, a PhoA signal sequence, OmpA signal sequence, and such are used; when using bacteria of the genus *Bacillus* as host cells, α-amylase signal sequence, subtilisin signal sequence, and such are used; when using yeast as host cells, MFα signal sequence, SUC2 signal sequence, and such are used; and when using animal cells as host cells, insulin signal sequence, α-interferon signal sequence, antibody molecule signal sequence, and such are used. Using expression vectors constructed in this manner to carry a polynucleotide encoding a polypeptide of the present invention can produce transformants.

Transformation of the above-described host cells can be carried out according to methods known in the art. Exemplary methods for transforming host cells are described in the following references: Proc. Natl. Acad. Sci. USA, 69:2110, 1972; Gene, 17:107, 1982; Molecular & General Genetics, 168:111, 1979; Methods in Enzymology, 194:182-187, 1991; Proc. Natl. Acad. Sci. USA, 75:1929, 1978; Cell Technology (Suppl. 8) New Cell Technology Experimental Protocol, 263-267, 1995, (Shujunsha); and Virology, 52:456, 1973.

Methods for introducing recombinant vectors into bacteria such as *E. coli* are not particularly limited, so long as they successfully introduce DNA into the selected bacteria. For example, calcium ion methods (Cohen, S. N. et al., Proc. Natl. Acad. Sci. USA, 69:2110, 1972) and electroporation methods may be used.

When yeast is used as the host, the methods for introducing recombinant vectors therein are not particularly limited, so long as they allow for successful introduction of DNA into yeast. For example, electroporation methods, spheroplast methods, and lithium acetate methods may be used.

When animal cells are used as the host, the methods for introducing recombinant vectors therein are not particularly limited, so long as they allow for successful introduction of DNA into the animal cells. For example, electroporation methods, calcium phosphate methods, and lipofection methods may be used.

When insect cells are used as the host, methods for introducing recombinant vectors into insect cells are not particularly limited, so long as they allow for successful introduction of DNA into the insect cells. For example, calcium phosphate methods, lipofection methods, and electroporation methods may be used.

Incorporation of a gene into a host can be confirmed, for example, by PCR, Southern hybridization, and Northern hybridization. Then, amplified products are subjected to, for example, agarose gel electrophoresis, polyacrylamide gel electrophoresis, or capillary electrophoresis, and stained with ethidium bromide, SYBR Green solution, etc. An amplified product detected as a single band indicates successful transformation. Amplified products may also be detected by performing PCR using primers pre-labeled with fluorescent dye and such. Furthermore, amplified products can be identified by fluorescence or enzymatic reactions after fixing them on a solid phase, such as a microplate.

The screening methods of the present invention can be carried out using the above-mentioned transformed cells. The screening methods that use the transformed cells of the present invention can be carried out as described below.

The screening methods of the present invention comprise the steps of culturing the aforementioned transformed cells together with a substrate peptide of Pim-1 and [$^{32}$P]-ATP, and measuring the phosphorylation activity of Pim-1 by measuring the incorporation of $^{32}$P into the substrate peptide. Such measurements are taken in the presence and absence of a test substance, and the results are compared to perform the screening. More specifically, the phosphorylation activity of Pim-1 is measured in the presence and absence of the test substance, and when phosphorylation activity is lower in the presence of the test compound than in its absence, the test substance is determined to have an inhibitory effect on Pim-1.

Alternatively, the screening methods of the present invention can be carried out by measuring apoptosis-inducing ability, instead of measuring the phosphorylation activity of Pim-1. More specifically, since Pim-1 inhibits apoptosis-inducing ability, when the effect of inhibiting this apoptosis-inducing ability is measured in the presence and absence of a test substance, a decrease in inhibition shows the test substance inhibits Pim-1 activity, has apoptosis-inducing ability, and is effective in preventing and treating cancer, and in potentiating anticancer agents.

Since Pim-1 is present in large amounts in solid cancer cells, compounds with inhibitory effects against Pim-1 may be compounds with preventive and therapeutic effects against cancer, or particularly against solid cancer. This therapeutic effect against cancer involves inhibiting the tumor-forming ability of cancer cells, and is brought forth by an apoptosis-inducing effect. Therefore, the above-mentioned screening methods can be used as methods of screening for apoptosis-inducing agents. In addition, the screening methods can be used as methods of screening for anticancer agent potentiators.

Furthermore, the screening methods of the present invention are methods of screening for substances that promote or inhibit the activity of serine/threonine kinase Pim-1, wherein the methods comprise the steps of contacting serine/threonine kinase Pim-1 or a partial peptide thereof, or a salt thereof, with a test substance, and then detecting the phosphorylation activity of serine/threonine kinase Pim-1.

Phosphorylation activity can be detected by using, as an indicator, the change in expression level of a reporter gene that is activated in response to binding of a serine/threonine kinase Pim-1 phosphorylation substrate. Alternatively, phosphorylation activity can be detected by using antibodies that recognize the phosphorylated form of the serine/threonine kinase Pim-1 phosphorylation substrate.

The following describes the detection of phosphorylation activity using, as an indicator, a change in the expression level of a reporter gene that is activated in response to the binding of a serine/threonine kinase Pim-1 phosphorylation substrate.

The binding sequence of the phosphorylation substrate peptide of Pim-1 is ligated to the reporter gene of the expression vector, and this vector is introduced into host cells. Further introduction of a Pim-1-expressing vector into the same host cells produces cells to which two expression vectors have been introduced. The aforementioned vectors can be used as Pim-1-expressing vectors.

Expression vectors for the reporter genes can be produced similarly to the Pim-1-expressing vectors, and the above-mentioned host cells can be used without any particular limitations.

The phosphorylation substrate peptides of Pim-1 used in the present invention will bind to the binding sequence when phosphorylated. Examples of such substrate peptides include c-Myb, Nuclear Factor of Activated T-cells (NFAT), and P21. For example, when c-Myb is phosphorylated, it binds to the binding sequence, and the reporter gene is expressed; thus, by detecting the expression of this reporter gene, it is possible to detect whether or not c-Myb is phosphorylated.

There are no particular limitations on the reporter genes, but preferably, the reporter genes are stable and their activity is easily determined. Examples of such reporter genes are DNAs encoding luciferase, β-galactosidase, β-glucuronidase, chloramphenicol acetyl transferase, peroxidase, HIS3 gene, green fluorescent protein (GFP), and such, but the reporter genes are not limited thereto. The reporter genes may have their original promoter, or the promoter portion may be substituted with a promoter derived from another gene. The reporter genes should be operably ligated downstream of a responsive element.

More specifically, in the above-mentioned screening methods, when the test substance has Pim-1-inhibiting activity, expression of the reporter gene is suppressed or inhibited. Thus, by detecting the expression of the reporter gene, it is possible to detect whether the test substance promotes or inhibits Pim-1 activity.

Next, detection of phosphorylation activity using antibodies that recognize the phosphorylated form of a serine/threonine kinase Pim-1 phosphorylation substrate will be described.

When using antibodies, for example, an antibody (primary antibody) that recognize a phosphorylated form of a phosphorylation substrate of Pim-1 is immobilized onto a plate. Separately, Pim-1 and the Pim-1 phosphorylation substrate peptide are mixed in a buffer solution in the presence or absence of a test substance, and this is usually incubated for two to four hours. This procedure causes the substrate peptide to be phosphorylated by Pim-1. Next, the buffer containing the substrate peptide is placed into the wells of the plate, and is incubated for a given period of time. This procedure allows the phosphorylated substrate peptide to bind to the primary antibody. The unphosphorylated substrate peptide does not bind to the primary antibody.

Since the phosphorylated substrate peptide is bound to the primary antibody, subsequent examination of binding with another antibody (the secondary antibody) against the substrate peptide enables examination of whether the substrate peptide is phosphorylated.

When using antibodies linked to a radioactive isotope, secondary antibody binding is detected by, for example, liquid scintillation counting or such. When using a complex formed between a secondary antibody and an enzyme, an enzyme-induced change in the substrate, such as the degree of coloring, is detected using an absorbance spectrometer. When using a secondary antibody linked to a fluorescent substance, detection is performed using a fluorescence spectrometer. Comparing the results obtained in the presence and absence of a test substance, enables examination of whether the test substance enhances or inhibits Pim-1 phosphorylation activity.

An example of a substrate for use is the P21 protein.

The antibodies that are used may be either polyclonal or monoclonal antibodies, as long as they can recognize the phosphorylated substrate protein, or unphosphorylated substrate protein. The antibodies can be produced according to conventionally known methods for producing antibodies or antisera using, for example, P21 protein (phosphorylated and unphosphorylated) as the antigen.

Next, the kits for screening of the present invention are described:

The screening kits of the present invention comprise Pim-1 or partial peptides thereof, or salts thereof. The screening kits of the present invention are used to screen for compounds that inhibit the activity of Pim-1 or partial peptides or salts thereof.

The screening kits of the present invention preferably comprise Pim-1 or partial peptides or salts thereof, a Pim-1 substrate peptide, and a phosphate donor for phosphorylating the substrate peptide.

The screening kits of the present invention also comprise the above-mentioned expression vectors or transformants. Preferably, screening kits comprising an expression vector or transformant also comprise a Pim-1 substrate peptide, and a phosphate donor for phosphorylation of the substrate peptide. The above-mentioned screening methods can be carried out using these screening kits.

Compounds that inhibit Pim-1 activity will become candidates for apoptosis-inducing pharmaceutical agents, and their application to the treatment and prevention of cancer, and as anticancer agent potentiators, may be considered.

The preventive and therapeutic agents for cancer, apoptosis-inducing agents, and anticancer agent potentiators of the present invention comprise compounds or salts thereof that inhibit the activity of Pim-1 or a partial peptide thereof, or a salt thereof. The above-mentioned screening methods or kits can be used to search for the compounds or salts thereof that inhibit the activity of Pim-1 or a partial peptide or salt thereof.

Specific examples of compounds that inhibit Pim-1 activity include polypeptides comprising an amino acid sequence that is identical to or substantially identical to a polypeptide comprising the amino acid sequence of SEQ ID No: 3. A polypeptide comprising the amino acid sequence of SEQ ID No: 3 is a polypeptide that has lost a kinase activity domain of Pim-1, comprising the amino acid sequence of SEQ ID No: 1, and is a polypeptide that has lost the amino acid residues at positions 1 to 80 of SEQ ID No: 1. A polypeptide comprising the amino acid sequence of SEQ ID No: 3 is a polypeptide that has lost a kinase activity domain. If this polypeptide is present, Pim-1 activity is inhibited. Therefore, this polypeptide can be used as a therapeutic and preventive agent for cancer, an apoptosis-inducing agent, and an anticancer agent potentiator. Compounds that inhibit Pim-1 activity include antibodies against Pim-1. Furthermore, compounds that inhibit Pim-1 activity include genes encoding Pim-1, or more specifically, double-stranded RNAs against a polynucleotide comprising the nucleotide sequence of SEQ ID No: 2 (hereinafter, sometimes referred to as "SiRNA"), and antisense oligonucleotides. The double-stranded RNAs are preferably short interference RNAs of 21 to 23 base pairs.

The polypeptides comprising the amino acid sequence of SEQ ID No: 3, and polypeptides that are substantially identical to the polypeptide comprising the amino acid sequence of SEQ ID No: 3 may be synthetic polypeptides.

An amino acid sequence that is substantially identical to the amino acid sequence of SEQ ID No: 3 is, for example, an amino acid sequence with a sequence homology to the amino acid sequence of SEQ ID No: 3 of approximately 50% or more, preferably approximately 60% or more, more preferably approximately 70% or more, even more preferably approximately 80% or more, especially preferably approximately 90% or more, and most preferably approximately 95% or more.

The polypeptides comprising the amino acid sequence of SEQ ID No: 3 include, for example, proteins comprising an amino acid sequence with one or two or more (for example, 1 to 50 or so, or preferably 1 to 30 or so) amino acid deletions in the amino acid sequence of SEQ ID No: 3; proteins comprising an amino acid sequence with one or two or more (for example, 1 to 100 or so, or preferably 1 to 30 or so) amino acid additions in the amino acid sequence of SEQ ID No: 3; proteins comprising an amino acid sequence with one or two or more (for example, 1 to 100 or so, or preferably 1 to 30 or so) amino acid insertions in the amino acid sequence of SEQ ID No: 3; peptides comprising an amino acid sequence with one or two or more (for example, 1 to 100 or so, or preferably 1 to 30 or so) amino acid substitutions in the amino acid sequence of SEQ ID No: 3; or proteins comprising an amino acid sequence with combinations of the above-mentioned alterations. The positions of these amino acid insertions, substitutions, and deletions are not particularly limited.

The C-terminus of proteins comprising the amino acid sequence of SEQ ID No: 3 may be a carboxyl group (—COOH), a carboxylate group (—COO), an amide group (—CONH$_2$), or an ester group (—COOR). R in the ester group includes, for example, an alkyl group of 1 to 6 carbon atoms, such as a methyl group, an ethyl group, an n-propyl group, an isopropyl group, or an n-butyl group; a cycloalkyl group of 3 to 8 carbon atoms such as a cyclopentyl group or a cyclohexyl group; an aryl group of 6 to 12 carbon atoms such as a phenyl group or an α-naphthyl group; a phenyl-alkyl group such as a benzyl group or a phenethyl group; an α-naphthyl-alkyl group such as an α-naphthylmethyl group; an aralkyl group of 7 to 14 carbon atoms; and a pivaloyloxymethyl group. When a protein represented by SEQ ID No: 3 has carboxyl groups (or carboxylate groups) besides the one at the C terminus, those carboxyl groups may be amidated or esterified. These esters include, for example, the esters described above for the C terminus. Furthermore, the proteins represented by SEQ ID No: 3 may be the following: proteins in which the amino group of the N-terminal amino acid residue (for example, the methionine residue) is protected by a protecting group (such as an acyl group of 1 to 6 carbon atoms, such as an alkanoyl group of 1 to 6 carbon atoms including a formyl group or an acetyl group); proteins in which the N-terminal glutamine residue, which is produced by cleavage in vivo, is converted to a pyroglutamate; or proteins in which the substituents on the side chains of amino acids in the molecule (—OH, —SH, an amino group, an imidazole group, an indole group, a guanidinio group, or such) are protected with appropriate protecting groups (for example, an acyl group of 1 to 6 carbon atoms, such as an alkanoyl group of 1 to 6 carbon atoms including a formyl group or an acetyl group); or conjugated proteins such as sugar-chain-linked so-called glycoproteins.

The polypeptide comprising the amino acid sequence of SEQ ID No: 3 may exist in the form of salts, and examples of such salts are similar to those described for Pim-1.

The polypeptides comprising the amino acid sequence of SEQ ID No: 3 can be synthesized by known peptide synthesis methods. Examples of peptide synthesis methods include methods similar to those described for Pim-1.

These polypeptides can also be produced by cleaving the above-mentioned Pim-1 with a suitable peptidase.

The polypeptides comprising the amino acid sequence of SEQ ID No: 3 can also be produced by culturing a transformant that has been transformed with an expression vector carrying a DNA encoding a polypeptide comprising the amino acid sequence of SEQ ID No: 3 (for example, a DNA comprising the nucleotide sequence of SEQ ID No: 4).

The polynucleotides encoding polypeptides comprising the amino acid sequence of SEQ ID No: 3 may be DNAs comprising the nucleotide sequence of SEQ ID No: 4, or any DNAs that comprise a nucleotide sequence that hybridizes under highly stringent conditions with a DNA comprising the nucleotide sequence of SEQ ID No: 4.

The DNAs that can hybridize under highly stringent conditions with the nucleotide sequence of SEQ ID No: 4 include, for example, DNAs comprising a nucleotide sequence having homology with the nucleotide sequence of SEQ ID NO: 4 of approximately 50% or greater, preferably approximately 60% or greater, more preferably approximately 70% or greater, even more preferably approximately 80% or greater, particularly preferably approximately 90% or greater, or most preferably approximately 95% or greater. Hybridization can be carried out by the methods described above. More preferably, hybridization can be performed under highly stringent conditions. Highly stringent conditions refer to the aforementioned conditions.

Means for cloning the DNAs that completely encode the polypeptides comprising the amino acid sequence of SEQ ID No: 3 include using synthetic DNA primers comprising portions of a nucleotide sequence encoding a polypeptide comprising the amino acid sequence of SEQ ID No: 3 to perform PCR amplification, or selection by hybridization of DNAs incorporated into appropriate vectors with a labeled DNA fragment encoding some or all regions of a polypeptide comprising the amino acid sequence of SEQ ID No: 3, or with a synthetic DNA. The hybridization methods used are described above. Changes to DNA nucleotide sequences are also carried out as described above.

The DNAs that encode the polypeptides comprising the amino acid sequence of SEQ ID No: 3, such as recombinant vectors carrying the polynucleotides comprising the nucleotide sequence of SEQ ID No: 4, can be produced by ligating the polynucleotide fragments downstream of promoters in appropriate expression vectors. The above-mentioned vectors and promoters are used.

In addition to the above-described promoters, the recombinant vectors may include known enhancers, splicing signals, poly(A) addition signals, selection markers, SV40 replication origins (sometimes abbreviated to "SV40orgdi" hereinafter), and such, as desired. Furthermore, if needed, the proteins encoded by a DNA of the present invention can also be expressed as fusion proteins with another protein (for example, glutathione-5-transferase and protein A). Such fusion proteins can be cleaved by using a site-specific protease to divide them into respective proteins.

The methods of using the above-mentioned recombinant vectors to transform host cells are the same as those described above. Furthermore, the above-mentioned host cells can be used.

Transformation of the above-mentioned host cells can be carried out according to methods well known in the art. These methods are the same as those described above.

The methods for obtaining polypeptides or salts thereof that comprise an amino acid sequence that is identical to or substantially identical to the amino acid sequence of SEQ ID No: 3 comprise the steps of culturing the above-mentioned host cells under conditions suitable for expressing the polypeptides, and collecting the polypeptides from the obtained cultures.

Specifically, the methods can be carried out by homogenizing the above-mentioned host cells, then extracting the homogenates using acid or such, and purifying the proteins from the extracts by known protein purification methods that combine chromatographic procedures such as reverse phase chromatography and ion exchange chromatography.

When a polypeptide is obtained in a free form, it can be converted to an appropriate salt by known methods. Furthermore, when it is obtained as a salt, it can be converted to a free form or to a different salt by known methods.

The polynucleotides of the present invention comprising nucleotide sequences encoding polypeptides comprising amino acid sequences that are identical to or substantially identical to the amino acid sequence of SEQ ID No: 3, the polynucleotides that are cDNAs that can hybridize to these polynucleotides, or recombinant vectors comprising these polynucleotides can be used as preventive and therapeutic agents for cancer, apoptosis-inducing agents, and anticancer agent potentiators.

For example, the above-mentioned effects on cancer patients and such are brought about by (A) administering a patient with an expression vector, in which an above-mentioned polynucleotide is controlled by a promoter that may function in a target cell, and expressing a polypeptide of the present invention in vivo, or (B) in a manner similar to that described above, introducing a polynucleotide of the present invention to cells removed from the patient, expressing the above-mentioned polypeptide in the cells, and then transplanting these cells to the patient. When using the above-mentioned polynucleotides for the aforementioned objectives, the polynucleotides can be administered by conventional techniques either alone, or after insertion into a suitable vector, such as a retrovirus vector, adenovirus vector, or adenovirus-associated viral vector.

The double-stranded RNAs against polynucleotides comprising the nucleotide sequence of SEQ ID No: 2 suppress the expression of genes comprising the same sequence. They therefore suppress the expression of polynucleotides comprising the nucleotide sequence of SEQ ID No: 2, and as a result, Pim-1 expression is suppressed, and Pim-1 activity can be inhibited. Such double-stranded RNAs are preferably short interference RNAs of 21 to 23 base pairs. As methods for preparing the double-stranded RNAs, conventionally known methods may be used without particular limitations, and for example, Silencer siRNA Construction Kit (Ambion) may be used for the preparation.

Double-stranded RNAs corresponding to the polynucleotides comprising the nucleotide sequence of SEQ ID No: 2 include, for example:

double-stranded RNAs that comprise a polynucleotide comprising the sequence of SEQ ID No: 9 (5'-aaugaugaagucgaa-gagauccccugucuc-3') and a polynucleotide comprising the sequence of SEQ ID No: 10 (5'-aagaucucuucgacuucaucaccu-gucuc-3');

double-stranded RNAs that comprise a polynucleotide comprising the sequence of SEQ ID No: 11 (5'-aaauc-uaaugagaugcugacaccugucuc-3') and a polynucleotide comprising the sequence of SEQ ID No: 12 (5'-aaugucagcaucucauuagauccugucuc-3'); and double-stranded RNAs that comprise a polynucleotide comprising the sequence of SEQ ID No: 13 (5'-aaauccauggaugg-uucuggaccugucuc-3') and a polynucleotide comprising the sequence of SEQ ID No: 14 (5-aauccagaaccauccauggauccu-gucuc-3).

The above-mentioned compounds that inhibit the activity of Pim-1, such as polypeptides comprising the amino acid sequence of SEQ ID No: 3, can be administered as is, or after formulation with a physiologically acceptable carrier, such as an auxiliary agent for enhancing intake. When using the above-mentioned polypeptides as preventive and therapeutic agents for cancer, apoptosis-inducing agents, or anticancer agent potentiators, it is preferable to use the polypeptide purified to preferably 90%, more preferably 95% or more, even more preferably 98% or more, and most preferably 99% or more. As necessary, the above-mentioned polypeptides can be administered orally as sugar-coated tablets, capsules, elixirs, microcapsules, or such, or parenterally as inhalants formed into aerosols, sterile solutions in water or other pharmaceutically acceptable solutions, or injectable solutions such as suspension agents.

For example, the polypeptide of the present invention can be mixed with physiologically acceptable carriers, flavoring agents, excipients, vehicles, preservatives, stabilizers, binders and such in a unit dosage form required in generally accepted pharmaceutical practice to produce pharmaceutical preparations. The amount of active ingredients in these preparations is adjusted so that appropriate doses can be obtained within specified ranges. Additives that can be mixed into tablets, capsules, and such include binders such as gelatin, corn starch, tragacanth, and gum arabic; excipients such as crystalline cellulose; swelling agents such as corn starch, gelatin, and alginic acid; lubricants such as magnesium stearate; sweeteners such as sucrose, lactose, and saccharin; and flavoring agents such as peppermint, akamono oil, and cherry. When the unit of prescription is in the form of a capsule, liquid carriers such as oils and fats may further be used together with the materials described above. Injections can be formulated by dissolving, suspending, or emulsifying a polypeptide of this invention in a sterile aqueous media or oleaginous liquid media ordinarily used to prepare injections. Examples of aqueous media for injection include physiological saline, and isotonic solutions containing glucose and other auxiliary agents, and they can be used in combination with appropriate solubilizers such as alcohols (for example, ethanol), polyalcohols (for example, propylene glycol, or polyethylene glycol), or nonionic surfactants [for example polysorbate 80, HCO-50 (polyoxyethylene (50 mol) adduct of hydrogenated castor oil)]. Examples of the oleaginous liquid media include sesame oil and soybean oil, and they may be used in combination with solubilizers such as benzyl benzoate or benzyl alcohol. The formulations may also include buffers (for example, phosphate buffer or sodium acetate buffer), analgesic agents (for example, benzalkonium chloride or procaine hydrochloride), stabilizers (for example, human serum albumin or polyethylene glycol), preservatives (for example, benzyl alcohol or phenol), or antioxidants. The liquid prepared for injection is normally packaged in an appropriate ampoule. The dose varies depending on the weight and age of the patient, and the method of administration, but one skilled in the art can appropriately select suitable doses.

Recombinant vectors in which the above-mentioned polynucleotides aer inserted are also prepared as described above, and are normally administered parenterally. Since the pharmaceutical preparations obtained in this manner are safe and have low toxicity, they can be administered to, for example, warm-blooded animals (such as humans, rats, mice, guinea pigs, rabbits, birds, sheep, pigs, cattle, horses, cats, dogs, monkeys, and chimpanzees), and can be used as preventive and therapeutic agents for cancer, apoptosis-inducing agents, and anticancer agent potentiators.

The above-mentioned therapeutic and preventive agents for cancer, and the anticancer agent potentiators, target cancers such as pancreatic cancer, esophageal cancer, gastric cancer, liver cancer, biliary tract cancer, spleen cancer, renal cancer, bladder cancer, uterine cancer, ovarian cancer, testicular cancer, thyroid cancer, brain tumor, and blood tumor, and these agents are particularly effective against solid cancers with a reduced oxygen concentration in the cells.

The therapeutic and preventive agents for cancer, apoptosis-inducing agents, and anticancer agent potentiators of the present invention, are administered to patients directly, or after formulation by known pharmaceutical methods. For example, they can be administered after formulation by appropriately combining with pharmaceutically acceptable carriers or media, more specifically, sterilized water and physiological saline, vegetable oils, emulsifiers, suspending agents, surfactants, stabilizers and so on. The agents can be administered to patients by methods well known to those skilled in the art, such as intraarterial injection, intravenous injection, subcutaneous injection, as well as intranasal, transbronchial, intramuscular, or oral administration. The dose varies depending on the weight and age of the patient, the method of administration, and such, but one skilled in the art can appropriately select suitable doses.

EXAMPLES

Hereinafter, the present invention is specifically illustrated below with reference to Examples, but is not to be construed as being limited thereto.

Example 1

The sensitivity of solid cancer cells to anticancer agents under low and normal oxygen partial pressures was investigated. Three types of solid pancreatic cancer cell lines (PCI-35 cells, KMP-4 cells, and PCI-43 cells) were used as the cells. For each type of cell, $2 \times 10^3$ cells were cultured for six hours in the presence of 50 µg/mL of cisplatin under low oxygen partial pressure (1% oxygen, 5% carbondioxide; hereinafter, the same values in the Examples) or normal oxygen partial pressure (20% oxygen, 5% carbondioxide; hereinafter, the same values in the Examples). After culturing, the cells were washed twice with physiological phosphate buffer (pH7.4) to prepare samples. Dulbecco's Modified Eagle's Medium/F12 was used as the medium for culturing (hereinafter, unless particularly specified, use of the same medium is assumed).

The cells described above were stained with propidium iodide (PI) and FITC-conjugated anti-anexin V, and FACS analysis was performed using FACS calibur (Becton Dickinson).

The results of FACS analysis are shown in FIG. 1. In FIG. 1, "Normoxia" means under normal oxygen partial pressure, and "Hypoxia" means under low oxygen partial pressure (the same hereinafter). The FACS analyses in the Examples can be described as staining of cells with PI and anti-anexin V, and sorting of cells based on the intensity of staining to show distributions such as those in FIG. 1. In the figures, the lower right quadrants represent early apoptotic cells, and the upper right quadrants represent late apoptotic cells. The lower left quadrants represent live cells. The proportion of apoptotic cells, which is the total of the lower right and upper right quadrants, is shown as a percentage. Hereinafter, the FACS analyses of are shown in the same manner.

As shown in FIG. 1, when the cells were cultured in the presence of cisplatin, induction of apoptosis under normoxia was approximately twice that under hypoxia for the three types of solid pancreatic cancer cell lines. More specifically, in the three types of solid pancreatic cancer cell lines, apoptosis induction was found to be more strongly inhibited under hypoxia than under normoxia.

Example 2

Figure 2:
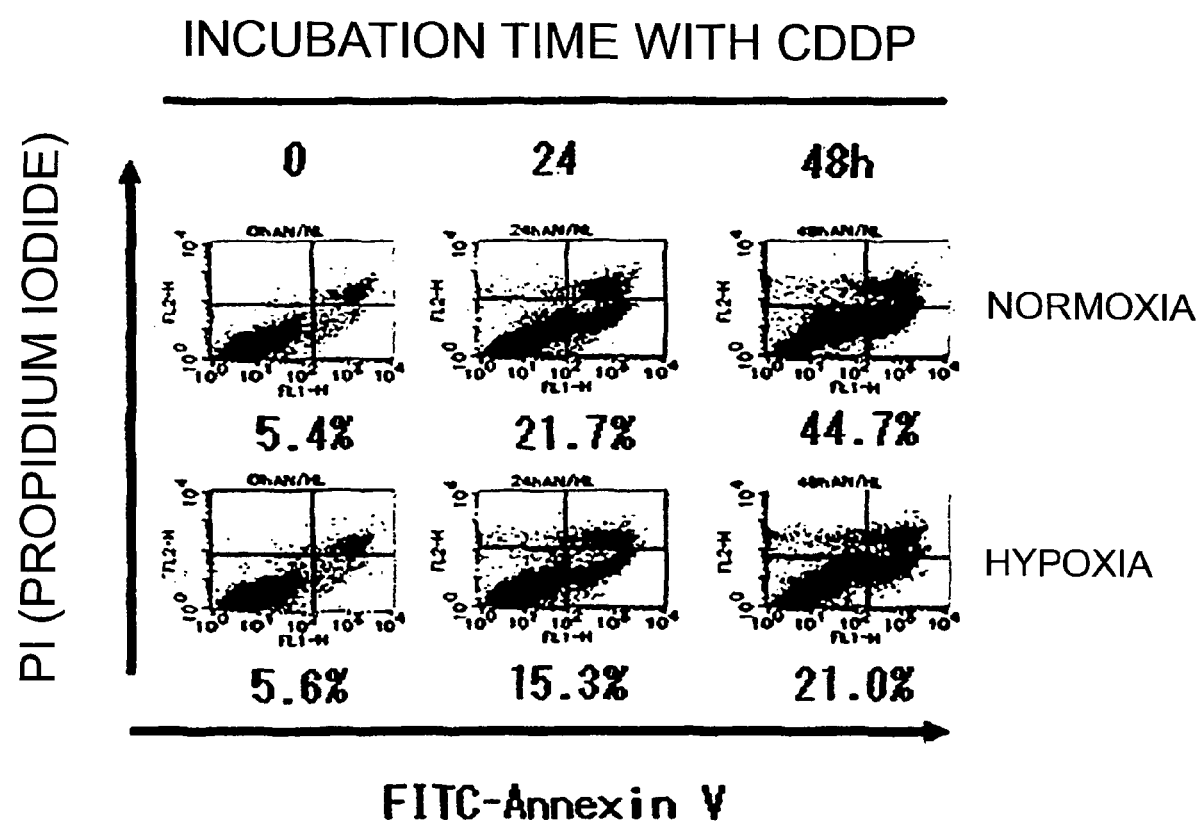
FIG. 2 shows the results of FACS analysis.

PCI-43 cells were cultured for up to 24 hours under the same conditions as in Example 1. Samples obtained before culturing, and after culturing for 12 hours and 24 hours were analyzed as in Example 1. The results are shown in FIG. 2. As shown in FIG. 2, apoptosis was induced by cisplatin as time progressed, but the proportion of apoptotic cells when cultured under hypoxia was approximately half that under normoxia.

The above-mentioned results show that each type of cell is more resistant to cisplatin-induced apoptosis under hypoxia than under normoxia.

Example 3

Using gemcitabine, adriamycin, and cisplatin, and using PCI-43 cells, measurements were made as in Example 1. The concentrations of gemcitabine and adriamycin were 0.1 to 1 μmol and 0.1 to 5 μmol, respectively. IC50 values were calculated from the measured results, as shown below.

The number of live cells was determined after 48 hours of treatment with various concentrations of anticancer agents, and the concentrations of anticancer agents needed to half the number of live cells present when the various anticancer agents were not added were defined as IC50 values. The results are shown in Table 1.

TABLE 1

| | IC50 (μM) | | |
|---|---|---|---|
| | Gemcitabine | Adriamycin | Cisplatin |
| Normoxia | 0.272 | 0.3 | 18.614 |
| Hypoxia | 1.565 | 1.9 | 27.742 |

As indicated in Table 1, for 50% apoptosis induction by the anticancer agents gemcitabine and adriamycin, higher concentrations of both were required under hypoxia than under normoxia, just as with cisplatin.

Example 4

Analyses were carried out on PCI-43 cells by culturing the cells as in Experiment 1, except that 2 μg/mL of anti-Fas antibody was used instead of cisplatin. Analyses were performed before culturing, and after culturing for 24 hours. The results are shown in FIG. 3.

Figure 3:
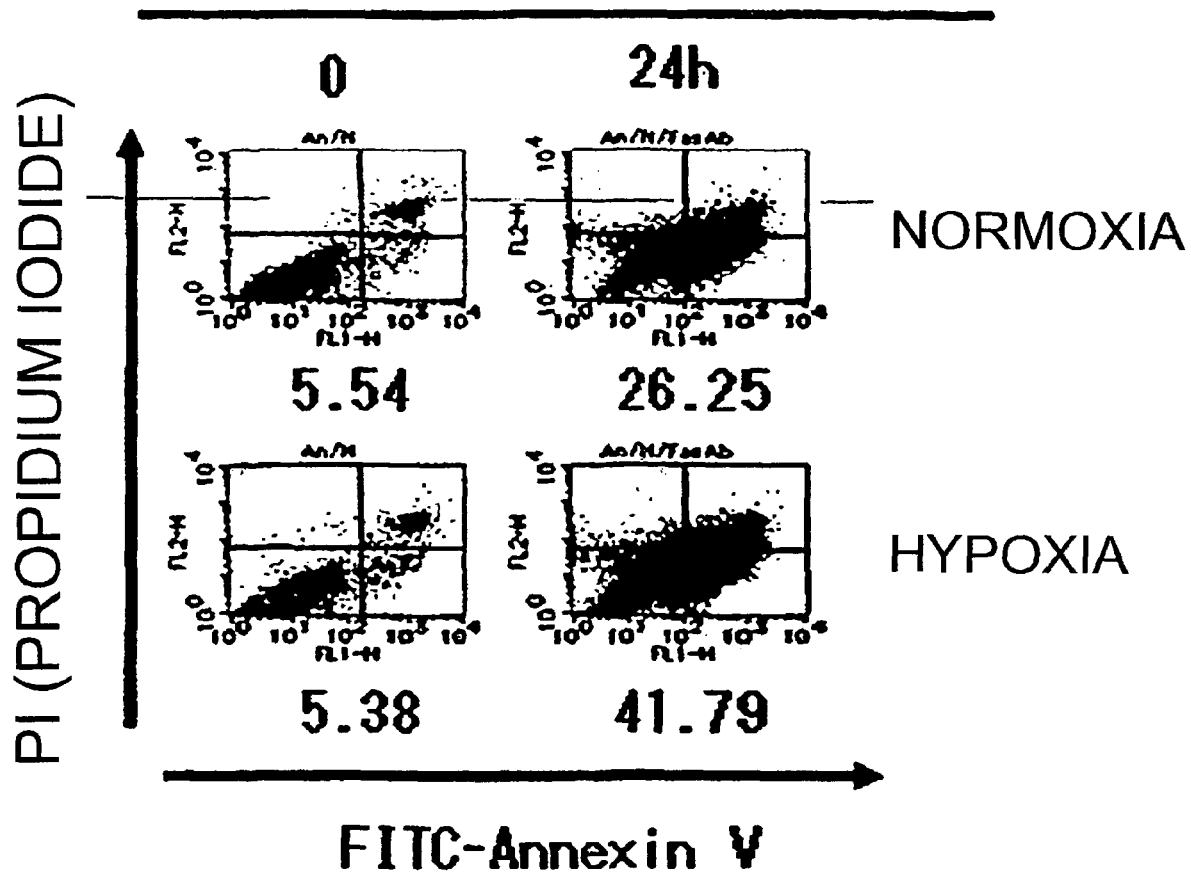
FIG. 3 shows the results of FACS analysis.

As shown in FIG. 3, PCI-43 cells were found to be more sensitive towards apoptosis induced by anti-Fas antibody under hypoxia than under normoxia.

Example 5

Various cancer cells were cultured under hypoxia and normoxia for 16 hours, and Pim-1 protein and Pim-1 mRNA in the respective cells were analyzed.

The cells used were HCT116 (colon cancer cell line), HePG2 (liver cancer cell line), KMP-4 (pancreatic cancer cell line), PCI-10 (pancreatic cancer cell line), PCI-35 (pancreatic cancer cell line), and PCI-43 (pancreatic cancer cell line). Each type of cell was cultured for 16 hours under hypoxia (1% oxygen, 5% carbondioxide), or normoxia (20% oxygen, 5% carbondioxide). RNA was extracted from the cultured cells using Trizol reagent, and proteins were extracted from the cultured cells using 1% NP-40 lysis buffer (50 μM Tris pH7.5, 150 nM NaCl, 2 μM EDTA, 1 μM EGTA, 50 μM NaF, 1 μM Na$_3$VO$_4$, 1 mM PMSF).

Proteins were detected by Western blotting. More specifically, the above-mentioned samples were electrophoresed through 12% polyacrylamide gels, and then blotted onto nitrocellulose membranes. The membranes were blocked with blocking buffer (5% skim milk, in physiological Tween-phosphate buffer), reacted with anti-Pim-1 antibody for one hour, then incubated with peroxidase-conjugated goat anti-mouse IgG secondary antibody, and detected using an ECL detection kit (Amersham).

Figure 4:
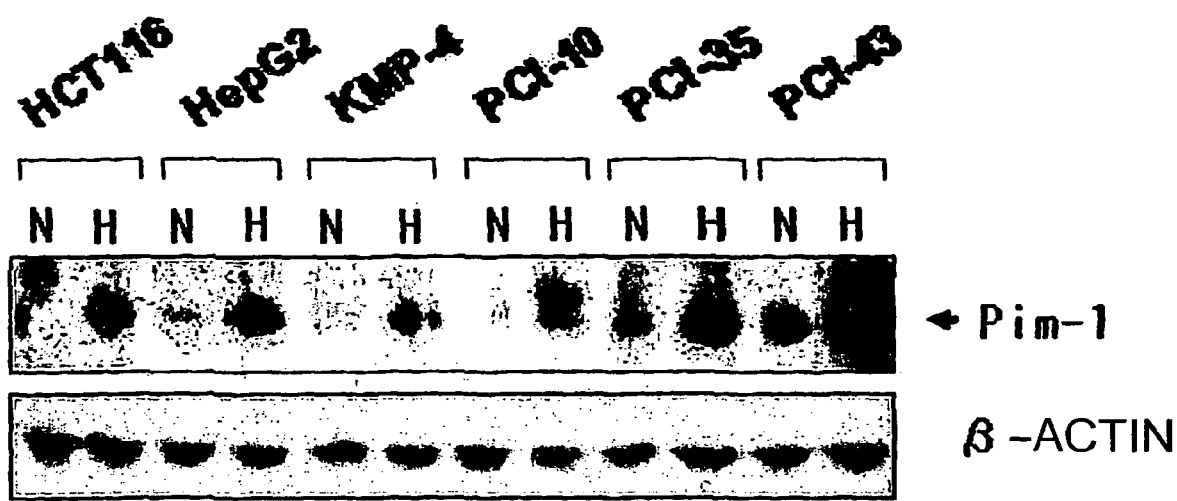
FIG. 4 shows the results of Western blotting to detect Pim-1 in various cells cultured under low and normal oxygen partial pressures.

The results are shown in FIG. 4. FIG. 4 shows the result of using Western blotting to detect Pim-1 obtained from culturing various cells under hypoxia and normoxia. In FIG. 4, N and H refer to the results of culturing under normoxia and hypoxia, respectively. As indicated in FIG. 4, in all examined cell lines, the amount of Pim-1 is greater when cultured under hypoxia than when cultured under normoxia.

Next, Northern blotting was performed to detect Pim-1 mRNA in various cells. cDNA fragments for Pim-1 detection were amplified by RT-PCR and used as probes for Northern blot analysis. The following were used as PCR primers.

pim-1

```
Forward: 5'-GGTTGGATGCTCTTGTCCAA-3'    (SEQ ID No: 5)

Reverse: 5'-CCTTCCAGAAGTCTTCTAT-3'     (SEQ ID No: 6)
```

Figure 5:
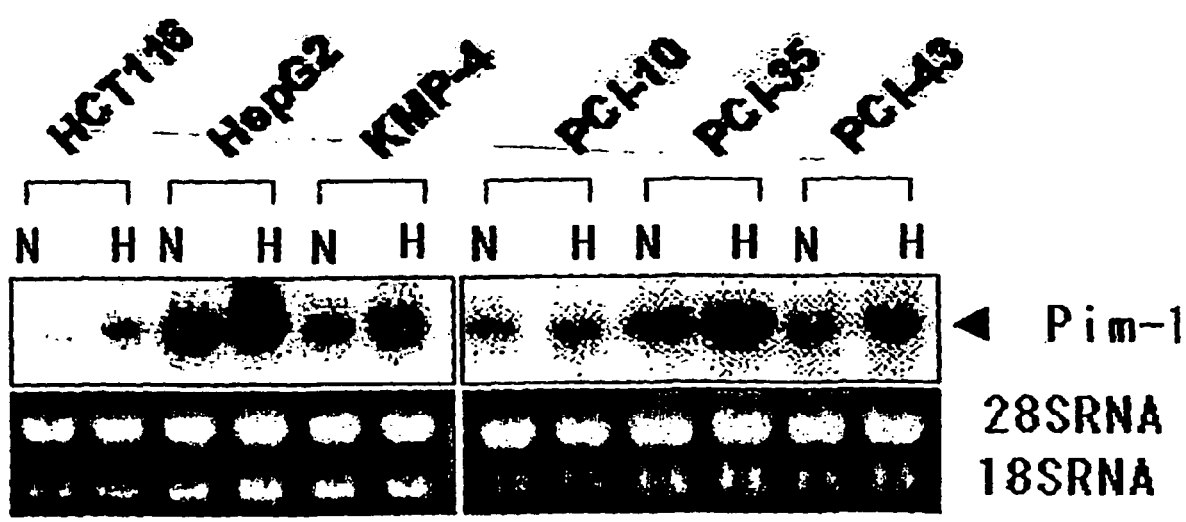
FIG. 5 shows the results of Northern blotting to detect Pim-1 mRNA in various cells cultured under low and normal oxygen partial pressures.

The results are shown in FIG. 5. FIG. 5 shows the result of using Northern blotting to detect Pim-1 mRNA obtained from culturing a variety of cells under hypoxia and normoxia. The graph shown at the bottom of FIG. 5 shows the intensity ratios obtained by using a scanner to read the Western blot analysis results shown above. FIG. 5 shows that in all examined cell lines, the amount of Pim-1 mRNA was greater when the cells were cultured under hypoxia than when cultured under normoxia.

The above-mentioned results show that Pim-1 is produced in larger amounts in cancer cells cultured under hypoxia than under normoxia.

Example 6

Figure 6:
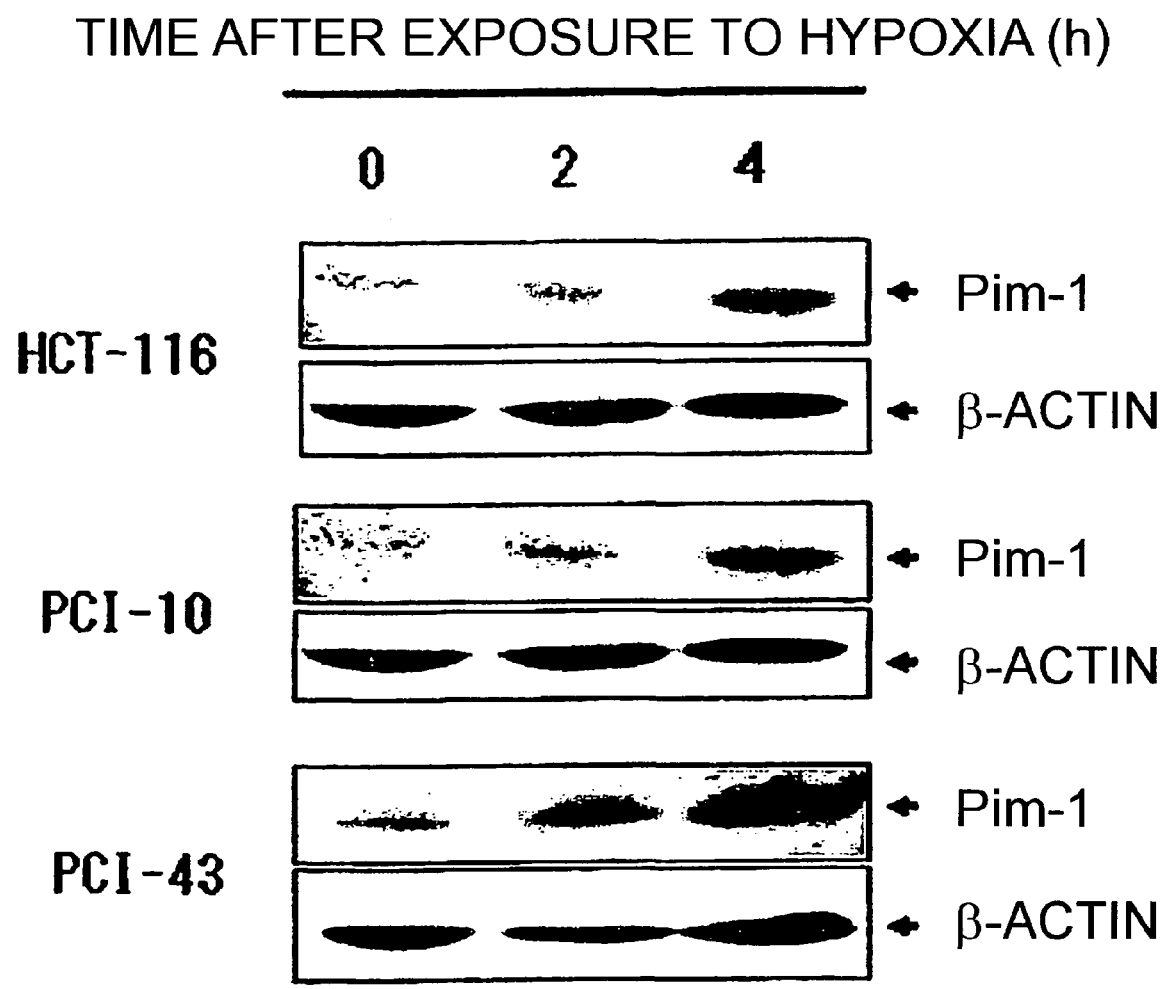
FIG. 6 shows the results of Western blotting to detect Pim-1 in three cell lines.

Expression of Pim-1 protein when various cancer cells were exposed to hypoxia was observed over time. The cells used were HCT116, PCI-10, and PCI-43. Cells were sampled before culturing the cells, and after exposure to hypoxia for two and four hours. The cells were treated in the same manner as in Example 5, and were subjected to Western blotting. The results are shown in FIG. 6. In FIG. 6, β-actin was used as the detection control. As shown in FIG. 6, in all of the three types of cells used, the amount of Pim-1 was found to increase with time after exposure to hypoxia.

Example 7

Figure 7:
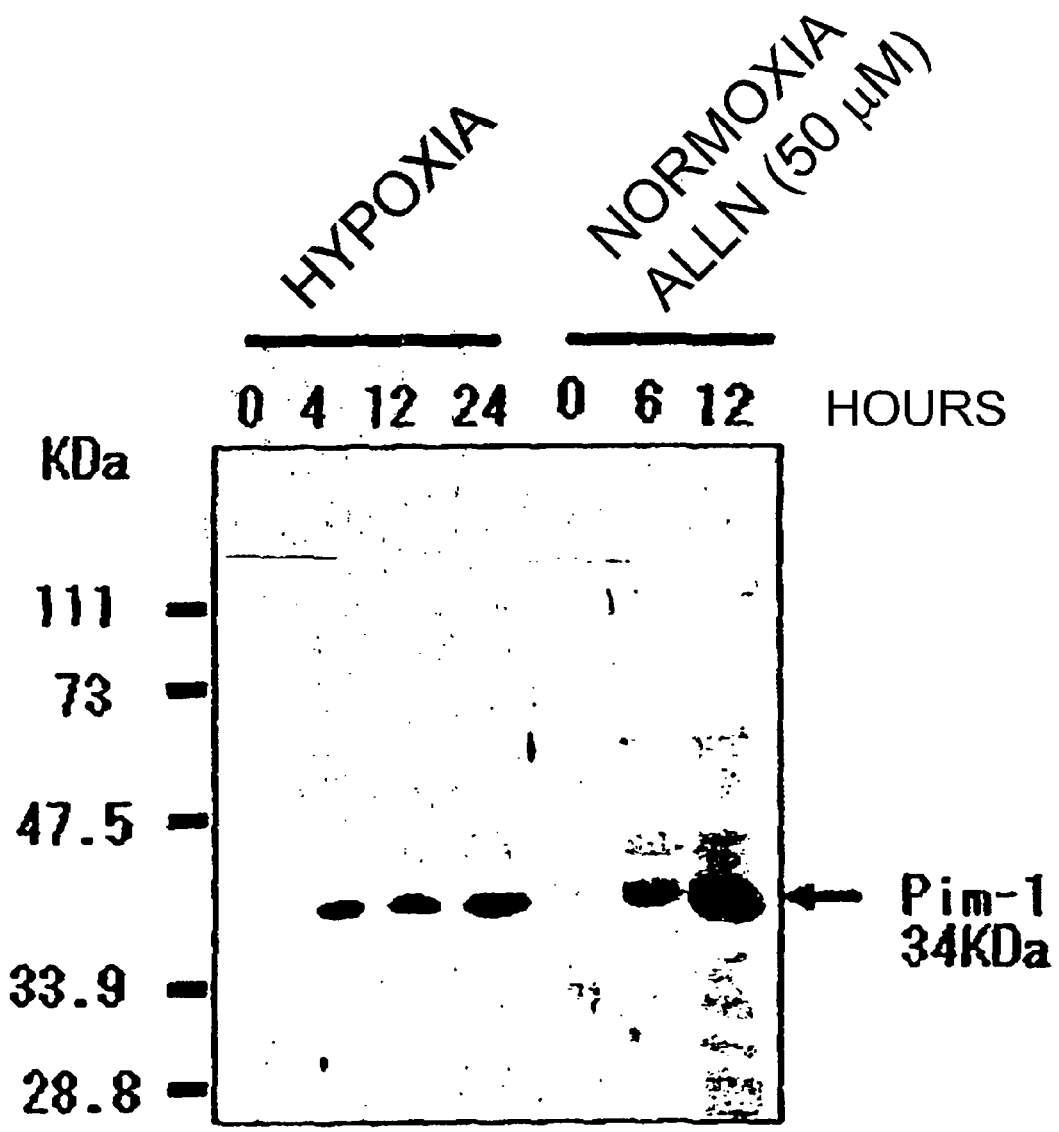
FIG. 7 shows the results of Western blotting to detect Pim-1 in the cells treated with a calpain inhibitor.

Whether or not Pim-1 is degraded by proteases under normoxia was investigated. PCI-43 cells were cultured under hypoxia and normoxia. Cells cultured under hypoxia were sampled before culturing, and after culturing for 4, 12, and 24 hours. Cells were treated in the same manner as in Example 5, and were subjected to Western blotting. Culturing under normoxia was carried out in media to which was added 50 μM of the proteasome inhibitor N-acetyl-L-leucinyl-L-leucinyl-L- norleucinal (ALLN). While culturing under normoxia, samples were obtained before culturing, and after culturing for 6 and 12 hours. Cells were treated in the same manner as in Example 5, and were subjected to Western blotting. The results are shown in FIG. 7. As shown in FIG. 7, when cultured under hypoxia, the amount of Pim-1 increases with time since exposure to hypoxia, and the amount of Pim-1 also increased with time under normoxia. This shows that Pim-1 protein is being degraded in the absence of the proteasome inhibitor.

Example 8

Figure 8:
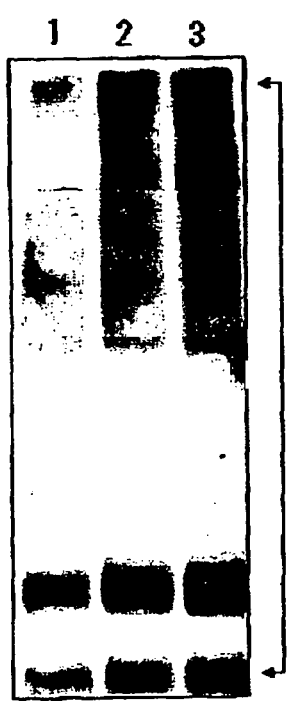
FIG. 8 shows the results of protein electrophoresis of ubiquitinated Pim-1.
Figure 8:

PCI-43 cells were cultured under normoxia in the presence of proteasome inhibitor ALLN. The cells were cultured for 16 hours, sampled, and after immunoprecipitation of ubiquitin, were analyzed by Western blotting. The same procedure was performed as in Example 5, except that anti-ubiquitin antibody and anti-Pim-1 antibody were used as primary antibodies. The concentrations of ALLN were 0, 50, and 100 µM. The results are shown in FIG. 8. In FIG. 8, the left-hand side shows the results of using anti-Pim-1 antibody as the primary antibody, and the right-hand side shows the results of using anti-ubiquitin antibody as the primary antibody. As FIG. 8 shows, since the samples reacted with anti-Pim-1 antibody, Pim-1 is bound to the immunoprecipitated ubiquitin. More specifically, Pim-1 is first ubiquitinated, and the proteasome uses ubiquitin as a marker, and degrades Pim-1.

Example 9

Examples 1 to 3 showed that the apoptosis-inducing ability caused by various anticancer agents is reduced in cancer cells under hypoxia. Furthermore, since Example 4 showed that large amounts of Pim-1 exist in cancer cells cultured under hypoxia, a dominant-negative Pim-1 transfectant was established in order to elucidate the role of Pim-1. The Pim-1 transfectant produces a peptide that is a wild-type Pim-1 lacking the kinase activity domain, or more specifically a peptide represented by SEQ ID No: 3.

The cDNA of the dominant-negative Pim-1 lacking the kinase activity domain was amplified from the RT product of mRNA purified from PCI-10 cells, and was cloned into pCR4-TOPO. The cDNA was sequenced using an ABI377 automated sequencer (Applied Biosystems), and a DyeDeoxy Terminator kit (Perkin-Elmer). The cloned cDNA fragment was then ligated into plasmid vector pcDNA3.1 (Invitrogen). The RT-PCR method is simply described below.

cDNA amplification of each RNA sample (5 µg) was carried out by incubation at 37° C. for one hour in a reaction mixture containing 75 mM KCl, 50 mM Tris-HCl (pH8.3), 3 mM MgCl$_2$, 10 mM dithiothreitol, 0.5 mM of each dNTP, 2 µM random primer, and 1000 U AMLV reverse transcriptase (Gibco BRL). cDNA was PCR amplified in a reaction mixture containing 50 mM KCl, 10 mM Tris-HCl (pH9.0), 2.5 mM MgCl$_2$, 0.1% Triton X-100, 200 µM of each dNTP, 10 µM of each specific primer, and 1 U of Taq polymerase (Gibco BRL). For PCR, 35 cycles (94° C., one minute; 60° C., one minute; and 72° C., two minutes) were performed in a DNA thermal cycler (Barnstead/Thermolyne).

The following were used as PCR primers:

dnpim-1

```
Forward: 5'-GTAGAATTCGCCACCATGCCTGCCTAATGGCACTCGAGTG-3'   (SEQ ID No: 7)

Reverse: 5'-GTACTATTTGCTGGGCCCCGGCGAC-3'                  (SEQ ID No: 8)
```

The obtained vector was transduced into PCI-43 cells using lipofectamine (Life Technologies). The transfectant was selected with 1,200 µg/mL of G-418, and then cloned by limiting dilution to obtain dominant-negative transfectants dnp3, dnp4, and dnp10. Next, the transfectant was maintained in the presence of 600 µg/mL of G-418.

Protein electrophoresis was performed on the obtained transformed cells. Sample preparation was carried out using 1% NP-40 lysis buffer (50 µM Tris pH7.5, 150 nM NaCl, 2 µM EDTA, 1 µM, EGTA, 50 µM NaF, 1 µM Na$_3$VO$_4$, and 1 µM PMSF).

As a control, protein electrophoresis was also performed on cells transformed with the vectors.

Figure 9:
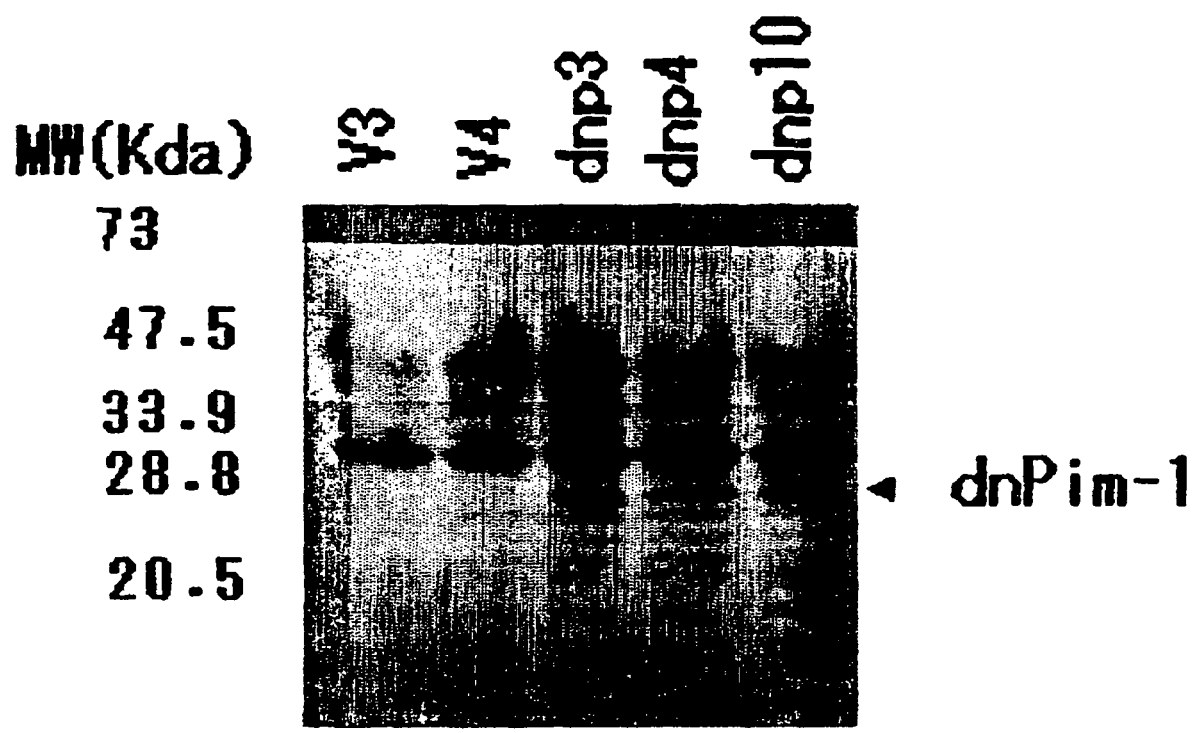
FIG. 9 shows the results of dominant negative Pim-1 expression in transformed cells.

The results are shown in FIG. 9. FIG. 9 shows the results of performing protein electrophoresis on the transformed cells. As FIG. 9 shows, peaks indicating the presence of Pim-1 lacking the kinase domain were found in dnp3, dnp4, and dnp10 (dnPim-1 in FIG. 9). This peak was not detected in cells transformed with just the vector alone (v3 and v4).

Example 10

Apoptosis-inducing ability was measured as in Example 1 for dnp3, dnp4, and dnp10 cells, and for v3 cells to which just the vector alone was introduced, which are the cells obtained in Example 9. The results are shown in FIG. 10.

Figure 10:
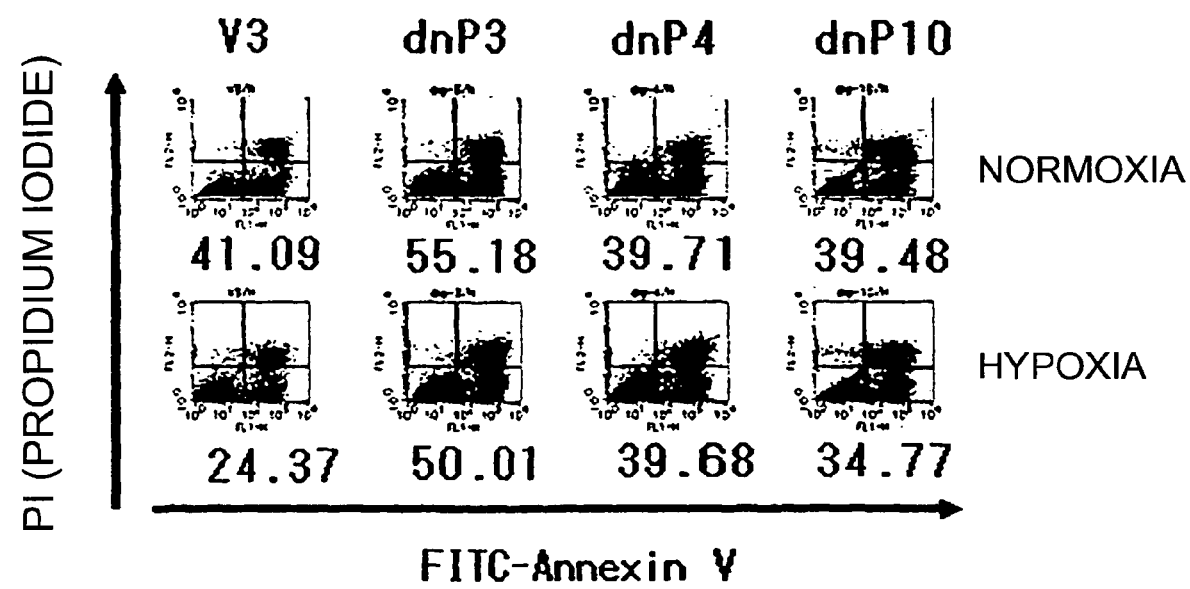
FIG. 10 shows the results of FACS analysis.

As shown in FIG. 10, when v3 was cultured in the presence of cisplatin, twice as much apoptosis was induced under normoxia than under hypoxia. In contrast, in dnp3, dnp4, and dnp10, which are dominant-negative Pim-1, no difference between culturing under normoxia and hypoxia was observed.

Example 11

Cells were cultured and analyses were performed as in Example 1, except 2 µg/mL of anti-Fas antibody was used instead of cisplatin. The analyses were performed before culturing, and after culturing for 24 hours. The results are shown in FIG. 11.

Figure 11:
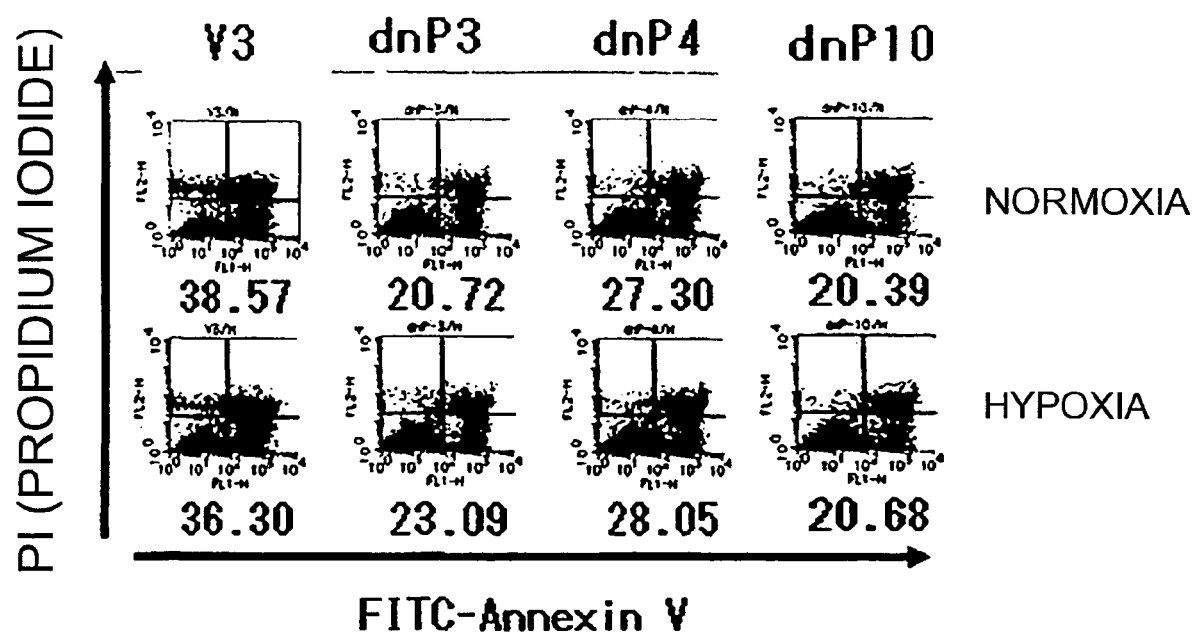
FIG. 11 shows the results of FACS analysis.

As shown in FIG. 11, the sensitivities of v3, dnp3, dnp4, and dnp10 to apoptosis induced by the anti-Fas antibody were the same under hypoxia and normoxia.

According to Examples 9 and 10, sensitivity to apoptosis induced by anticancer agents recovers when Pim-1 function is inhibited, but sensitivity to apoptosis induced by anti-Fas antibody under low-oxygen conditions does not recover. This indicates that Pim-1 is related to resistance to anticancer agents in pancreatic cancer cells.

Example 12

$5 \times 10^6$ cells each of v3, dnp3, dnp4, and dnp10 were injected subcutaneously to the right flank of SCID mice. After subcutaneous injection, tumor size was observed every three days up to the 21st day. Tumor size was measured by measuring the long and short diameters of the tumor with calipers, and calculating the volume using the following equation.

(short diameter)×(short diameter)×(long diameter)/2

Figure 12:
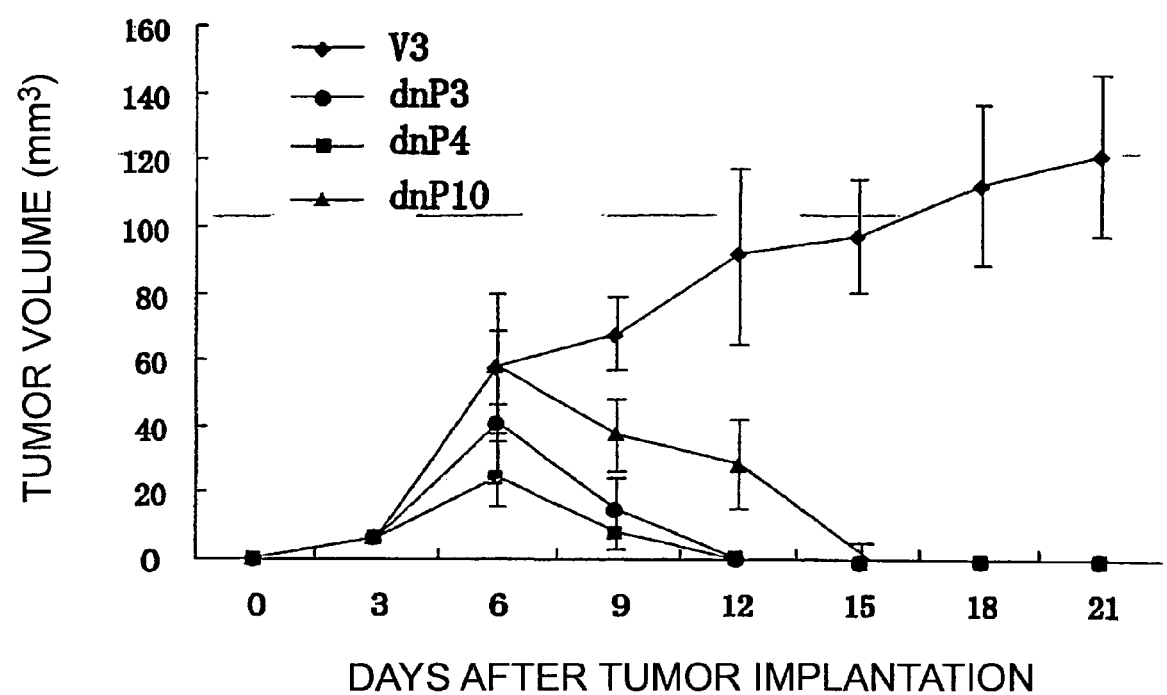
FIG. 12 is a graph showing the change in tumor size when various cells are administered.

The results are shown in FIG. 12. FIG. 12 is a graph showing the change in tumor size when various cells were administered. In the graph of FIG. 12, the horizontal axis shows the number of days since subcutaneous injection, and the vertical axis shows tumor size ($mm^3$). The graph of FIG. 12 shows the averages and standard deviations from experiments, each performed using 5 SCID mice. As shown in FIG. 12, as the days passed, tumor size increased in the group to which v3 was administered. In contrast, in groups that were administered with dnp3, dnp4, and dnp10, which carry dominant-negative Pim-1, the tumor size decreased from the 6th day after administration. Therefore, dominant-negative Pim-1 was found to lack tumor-forming ability.

Example 13

From mice used in Example 12, tumor tissues were removed six days after the subcutaneous injection, and the tissues were subjected to immunohistochemical staining: PCNA, and TUNEL staining of apoptotic cells. The results are shown in FIG. 13.

Figure 13:
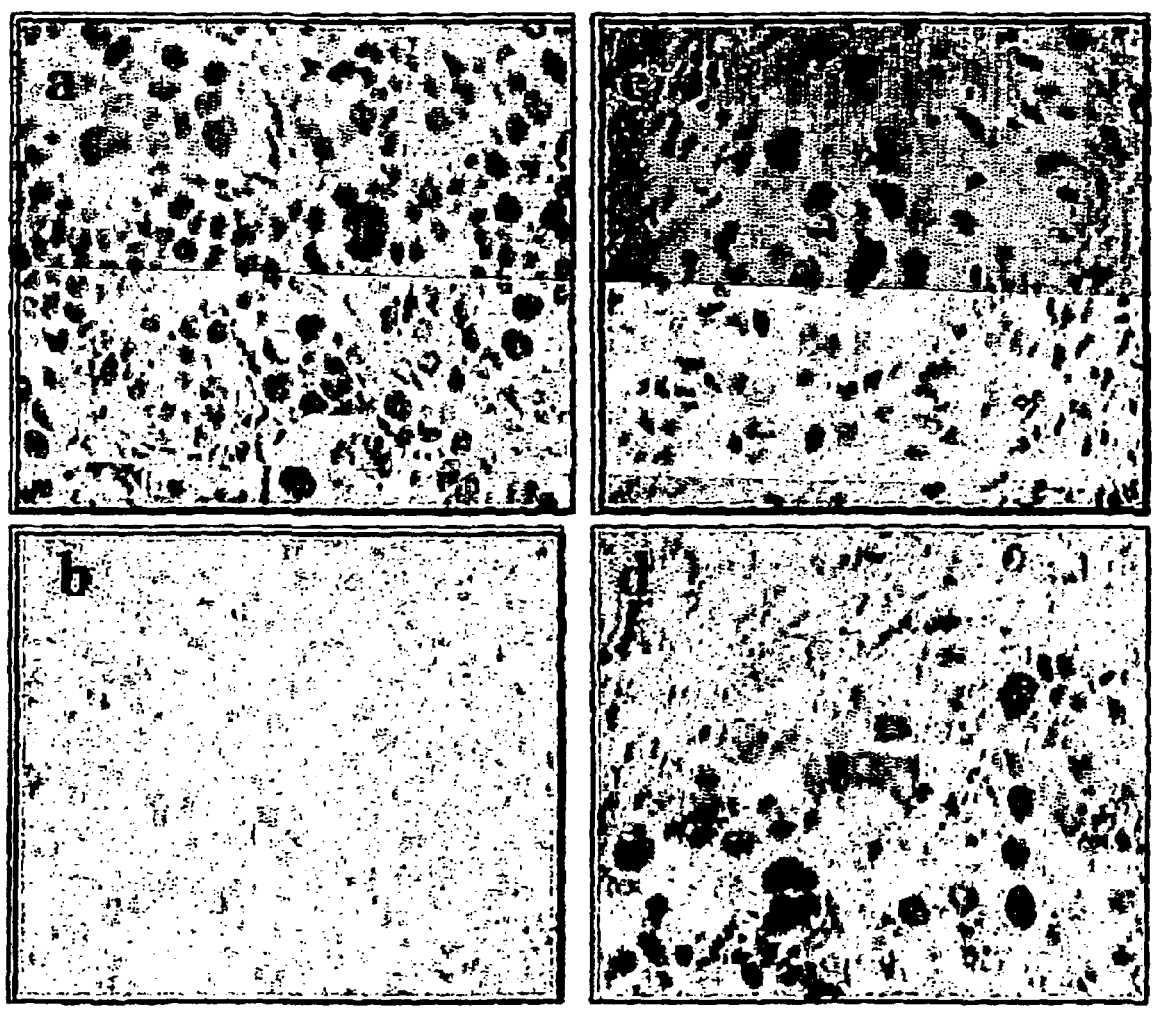
FIG. 13 is a set of photographs showing the results of immunohistochemical staining.

In FIG. 13, (a) shows the PCNA staining of tumor cells from mice subcutaneously injected with v3 cells; (b) shows the PCNA staining of tumor cells from mice subcutaneously injected with dnp4 cells; (c) shows the TUNEL staining of tumor cells from mice subcutaneously injected with v3; and (d) shows the TUNEL staining of tumor cells from mice subcutaneously injected with dnp4. As indicated in FIG. 13, significantly more cells were positively stained by PCNA in the v3 sample than in the dnp4 sample, while on the contrary, cells positively stained by TUNEL were found only in the dnp4 sample.

These results indicated that Pim-1 function is necessary for the formation of pancreatic cancer in vivo.

Example 14

Silencer siRNA Construction Kit (Ambion) was used to produce SiRNA comprising a polynucleotide comprising the nucleotide sequence of SEQ ID No: 9 and a polynucleotide comprising the nucleotide sequence of SEQ ID No: 10; SiRNA comprising a polynucleotide comprising the nucleotide sequence of SEQ ID No: 11 and a polynucleotide comprising the nucleotide sequence of SEQ ID No: 12; and SiRNA comprising a polynucleotide comprising the nucleotide sequence of SEQ ID No: 13 and a polynucleotide comprising the nucleotide sequence of SEQ ID No: 14 (these are referred to as Pim-1-RNASi-379, Pim-1-RNASi-784, and Pim-1-RNASi-848). SiRNA comprising a nucleotide sequence represented by SEQ ID NO: 15 was used as the control (this is referred to as GFP-control). PCI-43 cells ($2\times10^5$ cells) were plated into a 6-well plate, and incubated for 12 hours. Next SiRNA was introduced into these cells using Lipofectamine 2000 (Invitrogen), the cells were incubated for 24 hours, cultured for 48 hours with 50 µM of cisplatin under hypoxia and under normoxia, and FACS analysis was performed as in Example 1.

Figure 14:
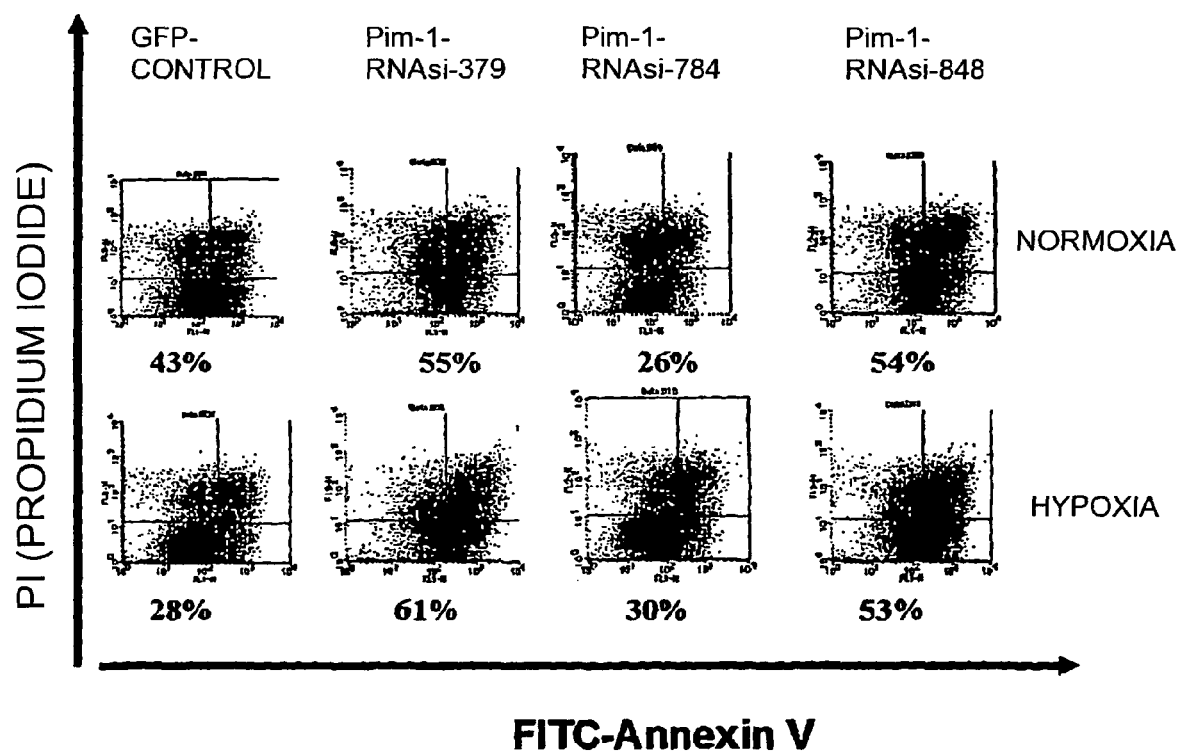
FIG. 14 shows the results of FACS analysis.

The results of FACS analysis are shown in FIG. 14. As indicated in FIG. 14, when the control cells were cultured in the presence of cisplatin under normoxia, approximately twice as much apoptosis was induced compared to under hypoxia. In contrast, when cultured in the presence of SiRNA, the results under normoxia and hypoxia did not differ.

Example 15

Human embryonic kidney 293 cell line carrying an expression vector in which a full length c-Myb is ligated to pcDNA3.1, and a c-Myb luciferase expression vector prepared by tandemly ligating five c-Myb binding sequence (5'-TAACGGTT-3', comprising the nucleotide sequence of SEQ ID No: 16) to a pTAL-Luc vector were mixed with pcDNA3.1-Pim-1 expression vector and a candidate compound, and then incubated. After incubation, dual luciferase assay reagent (Promega) was used to measure luciferase activity. Dominant-negative Pim-1 transfectant obtained in Example 9 was used as the candidate compound.

Although the results are not shown as a figure, luciferase activity was inhibited when dominant-negative Pim-1 transfectant was mixed, and this confirmed that this system can be used to search for compounds that inhibit Pim-1 activity.

As described in detail above, the amount of Pim-1 was increased in various cancer cells exposed to hypoxia, and Pim-1 was degraded under normoxia. Inhibiting the function of the Pim-1 gene using dominant-negative Pim-1 caused a decrease in both anticancer agent resistance, and tumor-forming ability.

Accordingly, inhibiting the function of the Pim-1 protein or the Pim-1 gene can bring out effects for cancer treatment, apoptosis induction, and potentiation of anticancer agents. Therefore, dominant-negative Pim-1 and compounds that inhibit the function of Pim-1 are effective for cancer treatment and such.

The invention claimed is:

1. A method of screening for a therapeutic agent for pancreatic cancer, wherein the method comprises the steps of:
   (a) contacting a test substance, or a salt thereof, with a purified serine/threonine kinase Pim-1 polypeptide or a partial peptide thereof having Pim-1 phosphorylation activity;
   (b) detecting the phosphorylation activity of the purified serine/threonine kinase Pim-1 polypeptide; and
   (c) identifying a test substance that inhibits the phosphorylation activity of the purified serine/threonine kinase Pim-1 polypeptide, wherein a test substance that inhibits the phosphorylation activity of the serine/threonine kinase Pim-1 polypeptide is a therapeutic agent for pancreatic cancer.

2. A method of screening for an apoptosis-inducing agent for pancreatic cancer, wherein the method comprises the steps of:
   (a) contacting a test substance, or a salt thereof, with a purified serine/threonine kinase Pim-1 polypeptide or a partial peptide thereof having Pim-1 phosphorylation activity;
   (b) detecting the phosphorylation activity of the purified serine/threonine kinase Pim-1 polypeptide; and
   (c) identifying a test substance that inhibits the phosphorylation activity of the purified serine/threonine kinase Pim-1 polypeptide, wherein a test substance that inhibits the phosphorylation activity of the serine/threonine kinase Pim-1 polypeptide is an apoptosis-inducing agent for pancreatic cancer.

3. A method of screening for an anticancer agent potentiator for pancreatic cancer, wherein the method comprises the steps of:
   (a) contacting a test substance, or a salt thereof, with a purified serine/threonine kinase Pim-1 polypeptide or a partial peptide thereof having Pim-1 phosphorylation activity;
   (b) detecting the phosphorylation activity of the punned serine/threonine kinase Pim-1 polypeptide; and
   (c) identifying a test substance that inhibits the phosphorylation activity of the purified serine/threonine kinase Pim-1 polypeptide, wherein a test substance that inhibits the phosphorylation activity of the serine/threonine kinase Pim-1 polypeptide is an anticancer agent potentiator for pancreatic cancer.

4. The method of claim 1, wherein the phosphorylation activity is detected by using, as an indicator, a change in the expression level of a reporter gene that is activated in response to binding of a serine/threonine kinase Pim-1 phosphorylation substrate.

5. The method of claim 1, wherein the phosphorylation activity is detected using an antibody that recognizes the phosphorylated form of the serine/threonine kinase Pim-1 phosphorylation substrate.

6. The method of claim 2, wherein the phosphorylation activity is detected by using, as an indicator, a change in the expression level of a reporter gene that is activated in response to binding of a serine/threonine kinase Pim-1 phosphorylation substrate.

7. The method of claim 2, wherein the phosphorylation activity is detected using an antibody that recognizes the phosphorylated form of the serine/threonine kinase Pim-1 phosphorylation substrate.

8. The method of claim 3, wherein the phosphorylation activity is detected by using, as an indicator, a change in the expression level of a reporter gene that is activated in response to binding of a serine/threonine kinase Pim-1 phosphorylation substrate.

9. The method of claim 3, wherein the phosphorylation activity is detected using an antibody that recognizes the phosphorylated form of the serine/threonine kinase Pim-1 phosphorylation substrate.

* * * * *

SEQUENCE LISTING

```
<160> NUMBER OF SEQ ID NOS: 16

<210> SEQ ID NO 1
<211> LENGTH: 313
<212> TYPE: PRT
<213> ORGANISM: Homo sapiens

<400> SEQUENCE: 1

Met Leu Leu Ser Lys Ile Asn Ser Leu Ala His Leu Arg Ala Ala Pro
 1               5                  10                  15

Cys Asn Asp Leu His Ala Thr Lys Leu Ala Pro Gly Lys Glu Lys Glu
            20                  25                  30
```

Pro Leu Glu Ser Gln Tyr Gln Val Gly Pro Leu Gly Ser Gly Gly
         35                  40                  45

Phe Gly Ser Val Tyr Ser Gly Ile Arg Val Ser Asp Asn Leu Pro Val
     50                  55                  60

Ala Ile Lys His Val Glu Lys Asp Arg Ile Ser Asp Trp Gly Glu Leu
 65                  70                  75                  80

Pro Asn Gly Thr Arg Val Pro Met Glu Val Val Leu Leu Lys Lys Val
                 85                  90                  95

Ser Ser Gly Phe Ser Gly Val Ile Arg Leu Leu Asp Trp Phe Glu Arg
                100                 105                 110

Pro Asp Ser Phe Val Leu Ile Leu Glu Arg Pro Glu Pro Val Gln Asp
             115                 120                 125

Leu Phe Asp Phe Ile Thr Glu Arg Gly Ala Leu Gln Glu Glu Leu Ala
         130                 135                 140

Arg Ser Phe Phe Trp Gln Val Leu Glu Ala Val Arg His Cys His Asn
145                 150                 155                 160

Cys Gly Val Leu His Arg Asp Ile Lys Asp Glu Asn Ile Leu Ile Asp
                165                 170                 175

Leu Asn Arg Gly Glu Leu Lys Leu Ile Asp Phe Gly Ser Gly Ala Leu
            180                 185                 190

Leu Lys Asp Thr Val Tyr Thr Asp Phe Asp Gly Thr Arg Val Tyr Ser
        195                 200                 205

Pro Pro Glu Trp Ile Arg Tyr His Arg Tyr His Gly Arg Ser Ala Ala
    210                 215                 220

Val Trp Ser Leu Gly Ile Leu Leu Tyr Asp Met Val Cys Gly Asp Ile
225                 230                 235                 240

Pro Phe Glu His Asp Glu Ile Ile Arg Gly Gln Val Phe Phe Arg
                245                 250                 255

Gln Arg Val Ser Ser Glu Cys Gln His Leu Ile Arg Trp Cys Leu Ala
                260                 265                 270

Leu Arg Pro Ser Asp Arg Pro Thr Phe Glu Glu Ile Gln Asn His Pro
        275                 280                 285

Trp Met Gln Asp Val Leu Leu Pro Gln Glu Thr Ala Glu Ile His Leu
    290                 295                 300

His Ser Leu Ser Pro Gly Pro Ser Lys
305                 310

<210> SEQ ID NO 2
<211> LENGTH: 942
<212> TYPE: DNA
<213> ORGANISM: Homo sapiens

<400> SEQUENCE: 2
atgctcttgt ccaaaatcaa ctcgcttgcc cacctgcgcg ccgcgccctg caacgacctg      60
cacgccacca agctggcgcc cggcaaggag aaggagcccc tggagtcgca gtaccaggtg     120
ggcccgctac tgggcagcgg cggcttcggc tcggtctact caggcatccg cgtctccgac     180
aacttgccgg tggccatcaa acacgtggag aaggaccgga tttccgactg gggagagctg     240
cctaatggca ctcgagtgcc catggaagtg gtcctgctga agaaggtgag ctcgggtttc     300
tccggcgtca ttaggctcct ggactggttc gagaggcccg acagtttcgt cctgatcctg     360
gagaggcccg agccggtgca agatctcttc gacttcatca cggaaagggg agccctgcaa     420
gaggagctgg cccgcagctt cttctggcag gtgctggagg ccgtgcggca ctgccacaac     480

-continued

| | |
|---|---|
| tgcggggtgc tccaccgcga catcaaggac gaaaacatcc ttatcgacct caatcgcggc | 540 |
| gagctcaagc tcatcgactt cgggtcgggg gcgctgctca aggacaccgt ctacacggac | 600 |
| ttcgatggga cccgagtgta tagccctcca gagtggatcc gctaccatcg ctaccatggc | 660 |
| aggtcggcgg cagtctggtc cctggggatc ctgctgtatg atatggtgtg tggagatatt | 720 |
| cctttcgagc atgacgaaga gatcatcagg ggccaggttt tcttcaggca gagggtctct | 780 |
| tcagaatgtc agcatctcat tagatggtgc ttggccctga gaccatcaga taggccaacc | 840 |
| ttcgaagaaa tccagaacca tccatggatg caagatgttc tcctgcccca ggaaactgct | 900 |
| gagatccacc tccacagcct gtcgccgggg cccagcaaat ag | 942 |

<210> SEQ ID NO 3
<211> LENGTH: 233
<212> TYPE: PRT
<213> ORGANISM: Homo sapiens

<400> SEQUENCE: 3

Pro Asn Gly Thr Arg Val Pro Met Glu Val Val Leu Leu Lys Lys Val
1               5                   10                  15

Ser Ser Gly Phe Ser Gly Val Ile Arg Leu Leu Asp Trp Phe Glu Arg
            20                  25                  30

Pro Asp Ser Phe Val Leu Ile Leu Glu Arg Pro Glu Pro Val Gln Asp
        35                  40                  45

Leu Phe Asp Phe Ile Thr Glu Arg Gly Ala Leu Gln Glu Glu Leu Ala
    50                  55                  60

Arg Ser Phe Phe Trp Gln Val Leu Glu Ala Val Arg His Cys His Asn
65                  70                  75                  80

Cys Gly Val Leu His Arg Asp Ile Lys Asp Glu Asn Ile Leu Ile Asp
                85                  90                  95

Leu Asn Arg Gly Glu Leu Lys Leu Ile Asp Phe Gly Ser Gly Ala Leu
            100                 105                 110

Leu Lys Asp Thr Val Tyr Thr Asp Phe Asp Gly Thr Arg Val Tyr Ser
        115                 120                 125

Pro Pro Glu Trp Ile Arg Tyr His Arg Tyr His Gly Arg Ser Ala Ala
    130                 135                 140

Val Trp Ser Leu Gly Ile Leu Leu Tyr Asp Met Val Cys Gly Asp Ile
145                 150                 155                 160

Pro Phe Glu His Asp Glu Glu Ile Ile Arg Gly Gln Val Phe Phe Arg
                165                 170                 175

Gln Arg Val Ser Ser Glu Cys Gln His Leu Ile Arg Trp Cys Leu Ala
            180                 185                 190

Leu Arg Pro Ser Asp Arg Pro Thr Phe Glu Glu Ile Gln Asn His Pro
        195                 200                 205

Trp Met Gln Asp Val Leu Leu Pro Gln Glu Thr Ala Glu Ile His Leu
    210                 215                 220

His Ser Leu Ser Pro Gly Pro Ser Lys
225                 230

<210> SEQ ID NO 4
<211> LENGTH: 702
<212> TYPE: DNA
<213> ORGANISM: Homo sapiens

<400> SEQUENCE: 4

| | |
|---|---|
| cctaatggca ctcgagtgcc catggaagtg gtcctgctga agaaggtgag ctcgggtttc | 60 |

-continued

| | |
|---|---|
| tccggcgtca ttaggctcct ggactggttc gagaggcccg acagtttcgt cctgatcctg | 120 |
| gagaggcccg agccggtgca agatctcttc gacttcatca cggaaagggg agccctgcaa | 180 |
| gaggagctgg cccgcagctt cttctggcag gtgctggagg ccgtgcggca ctgccacaac | 240 |
| tgcggggtgc tccaccgcga catcaaggac gaaaacatcc ttatcgacct caatcgcggc | 300 |
| gagctcaagc tcatcgactt cgggtcgggg gcgctgctca aggacaccgt ctacacggac | 360 |
| ttcgatggga cccgagtgta tagccctcca gagtggatcc gctaccatcg ctaccatggc | 420 |
| aggtcggcgg cagtctggtc cctggggatc ctgctgtatg atatggtgtg tggagatatt | 480 |
| cctttcgagc atgacgaaga gatcatcagg ggccaggttt tcttcaggca gagggtctct | 540 |
| tcagaatgtc agcatctcat tagatggtgc ttggccctga gaccatcaga taggccaacc | 600 |
| ttcgaagaaa tccagaacca tccatggatg caagatgttc ccctgcccca ggaaactgct | 660 |
| gagatccacc tccacagcct gtcgccgggg cccagcaaat ag | 702 |

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 5
ggttggatgc tcttgtccaa                                                20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:PCR primer

<400> SEQUENCE: 6
ccttccagaa gtcttctat                                                 19

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence:PCR primer

<400> SEQUENCE: 7
gtagaattcg ccaccatgcc tgcctaatgg cactcgagtg                          40

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 8
gtactatttg ctgggccccg gcgac                                          25

<210> SEQ ID NO 9
<211> LENGTH: 29
<212> TYPE: RNA
<213> ORGANISM: Artificial Sequence
<220> FEATURE:
<223> OTHER INFORMATION: Description of Artificial Sequence:short
      interference RNA
```

```
<400> SEQUENCE: 9
aaugaugaag ucgaagagau cccugucuc                                    29

<210> SEQ ID NO 10
<211> LENGTH: 29
<212> TYPE: RNA
<213> ORGANISM: Artificial Sequence
<220> FEATURE:
<223> OTHER INFORMATION: Description of Artificial Sequence:short
      interference RNA

<400> SEQUENCE: 10
aagaucucuu cgacuucauc accugucuc                                    29

<210> SEQ ID NO 11
<211> LENGTH: 29
<212> TYPE: RNA
<213> ORGANISM: Artificial Sequence
<220> FEATURE:
<223> OTHER INFORMATION: Description of Artificial Sequence:short
      interference RNA

<400> SEQUENCE: 11
aaaucuaaug agaugcugac accugucuc                                    29

<210> SEQ ID NO 12
<211> LENGTH: 29
<212> TYPE: RNA
<213> ORGANISM: Artificial Sequence
<220> FEATURE:
<223> OTHER INFORMATION: Description of Artificial Sequence:short
      interference RNA

<400> SEQUENCE: 12
aaugucagca ucucauuaga uccugucuc                                    29

<210> SEQ ID NO 13
<211> LENGTH: 29
<212> TYPE: RNA
<213> ORGANISM: Artificial Sequence
<220> FEATURE:
<223> OTHER INFORMATION: Description of Artificial Sequence:short
      interference RNA

<400> SEQUENCE: 13
aaauccaugg augguucugg accugucuc                                    29

<210> SEQ ID NO 14
<211> LENGTH: 29
<212> TYPE: RNA
<213> ORGANISM: Artificial Sequence
<220> FEATURE:
<223> OTHER INFORMATION: Description of Artificial Sequence:short
      interference RNA

<400> SEQUENCE: 14
aauccagaac cauccaugga uccugucuc                                    29

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence:short
      interference RNA

<400> SEQUENCE: 15
```

```
ggcuacgucc aggagcgcac c                                              21
```

<210> SEQ ID NO 16
<211> LENGTH: 8
<212> TYPE: DNA
<213> ORGANISM: Artificial Sequence
<220> FEATURE:
<223> OTHER INFORMATION: Description of Artificial Sequence:primer

<400> SEQUENCE: 16

```
taacggtt                                                              8
```